United States Patent [19]

McGrogan et al.

[11] Patent Number: 4,939,093
[45] Date of Patent: Jul. 3, 1990

[54] HUMAN IL-2 LIKE POLYPEPTIDES, DNA SEQUENCES AND RECOMBINANT DNA MOLECULES THEREFORE AND METHODS FOR THE PRODUCTION AND USE THEREOF

[75] Inventors: Michael P. McGrogan, Albany; Ernest S. Kawasaki, Richmond; Michael V. Doyle, Oakland; David F. Mark, Hercules, all of Calif.

[73] Assignee: Cetus Corporation, Emeryville, Calif.

[21] Appl. No.: 236,296

[22] Filed: Aug. 23, 1988

Related U.S. Application Data

[63] Continuation of Ser. No. 9,999, Feb. 2, 1987, abandoned, which is a continuation of Ser. No. 457,594, Jan. 13, 1983, abandoned, which is a continuation-in-part of Ser. No. 426,059, Sep. 28, 1982, abandoned.

[51] Int. Cl.$^5$ .................. C12N 1/20; C12N 15/00; C12P 21/00; C12P 19/34
[52] U.S. Cl. ............................. 435/252.3; 435/69.52; 435/91; 435/172.3; 435/240.1; 435/240.2; 536/27; 935/4; 935/6; 935/21; 935/70; 935/72
[58] Field of Search ................ 435/68, 70, 71, 91, 435/172.1, 172.3, 320, 6, 240.1, 240.2, 252.3, 252.31–252.35, 11, 13, 19, 21, 29, 72, 73, 79, 4.6, 69.52; 536/27

[56] References Cited

U.S. PATENT DOCUMENTS 4,401,756  8/1983  Gillis ..................................... 435/68
4,411,993 10/1983  Gillis ..................................... 435/68
4,564,593  1/1986  Tsukanmoto et al. ................. 435/91
4,738,927  4/1988  Taniguchi et al. ................... 435/243

FOREIGN PATENT DOCUMENTS 0088195  9/1983  European Pat. Off. ......... 435/172.3
2063882 10/1981  United Kingdom ............. 435/172.3

OTHER PUBLICATIONS

*Gene Expression*, vol. 2, Lewin, John Wiley & Sons, Ltd., London, 1974, p. 161.
Ting et al., in *Genetic Engineering Techniques*, Huang et al. (ed.), Academic Press, 1982, pp. 225–239.
Lin et al., J. Biol. Chem., 257: 1587 (1982).
Efrat et al., Nature, 297: 236 (1982).
Bleackley et al., J. Immunol., 127: 2432 (1981).
Maxam et al., Methods in Enzymology, 65: 499 (1980).
Pawlowski et al., J. Biol. Chem., 250: 2135 (1975).
Kennell; Progr. Nucl. Acid Res. Mol. Biol., 11: 259–301 (1971).
Wiles et al.; Somatic Cell and Mol. Genet., 14, 31 (1988).

*Primary Examiner*—James Martinell
*Attorney, Agent, or Firm*—Kate H. Murashige; Shyamala T. Rajender; Albert P. Halluin

[57] ABSTRACT

DNA sequences and recombinant DNA molecules which encode human IL-2 IL-2 like polypeptides, hosts transformed with vectors carrying the DNA sequences as inserts, methods for their production and therapeutic formulations utilizing the IL-2 and IL-2 like polypeptides are provided.

12 Claims, 23 Drawing Sheets

FIG.4-1

```
  1
    TC CTG AGG AAC AGA CTT AAG TAT GCC CTG ACA GGA GAT GAA GTA AAG AAG ATT TGC ATG
                                                                              met
 60
    CAG CGG TTC ATT AAA ATC GAT GGC AAG GTC CGA ACT GAT ATA ACC TAC CCT GCT GGA TTC
    gln arg phe ile lys ile asp gly lys val arg thr asp ile thr tyr pro ala gly phe
120
    ATG GAT GTC ATC AGC ATT GAC AAG ACG GGA GAG AAT TTC CGT CTG ATC TAT GAC ACC AAG
    met asp val ile ser ile asp lys thr gly glu asn phe arg leu ile tyr asp thr lys
180
    GGT CGC TTT GCT GTA CAT CGT ATT ACA CCT GAG GAG GCC AAG TAC AAG TTG TGC AAA GTG
    gly arg phe ala val his arg ile thr pro glu glu ala lys tyr lys leu cys lys val
240
    AGA AAG ATC TTT GTG GGC ACA AAA GGA ATC CCT CAT CTG GTG ACT CAT GAT GCC CGC ACC
    arg lys ile phe val gly thr lys gly ile pro his leu val thr his asp ala arg thr
300
    ATC CGC TAC CCC GAT CCC CTC ATC AAG GTG AAT GAT ACC ATT CAG ATT GAT TTA GAG ACT
    ile arg tyr pro asp pro leu ile lys val asn asp thr ile gln ile asp leu glu thr
```

```
360
GGC AAG ATT ACT GAT TTC ATC AAG TTC GAC ACT GGT AAC CTG TGT ATG GTG ACT GGA GGT
gly lys ile thr asp phe ile lys phe asp thr gly asn leu cys met val thr gly gly 420
GCT AAC CTA GGA AGA ATT GGT GTG ATC AAC AGA GAG AGG CAC CCT GGA TCT TTT GAC
ala asn leu gly arg ile gly val ile thr asn arg glu arg his pro gly ser phe asp 480
GTG GTT CAC GTG AAA GAT GCC AAT GGC AAC AGC TTT GCC ACT CGA CTT TCC AAC ATT TTT
val val his val lys asp ala asn gly asn ser phe ala thr arg leu ser asn ile phe 540
GTT ATT GGC AAG GGC AAC AAA CCA TGG ATT TCT CTT CCC CGA GGA AAG GGT ATC CGC CTC
val ile gly lys gly asn lys pro trp ile ser leu pro arg gly lys gly ile arg leu 600
ACC ATT GCT GAA GAG AGA GAC AAA AGA CTG GCG GCC AAA CAG AGC AGT GGG TGA AAT GGG
thr ile ala glu glu arg asp lys arg leu ala ala lys gln ser ser gly ***

660
TCC CTG GTG ACA TGT CAG ATC TTT GTA CGT AAT TAA AAA TAT TGT GGC AGG ATT AAT AGC
```

FIG.4-2

```
                              90         100        110        120
                             GTCC GAACTGATAT AACCTACCCT GCTGGATTCA
       130        140        150        160        170        180
  TGGATGTCAT CAGCATTGAC AAGACGGGAG AGAATTTCCG TCTGATCTAT GACACCAAGG
       190        200        210        220        230        240
  GTCGCTTTGC TGTACATCGT ATTACACCTG AGGAGGCCAA GTACAAGTTG TGCAAAGTGA
       250        260        270        280        290        300
  GAAAGATCTT TGTGGGCACA AAAGGAATCC CTCATCTGGT GACTCATGAT GCCCGCACCA
       310        320        330        340        350        360
  TCCGCTACCC CGATCCCCTC ATCAAGGTGA ATGATACCAT TCAGATTGAT TTAGAGACTG
       370        380        390        400        410        420
  GCAAGATTAC TGATTTCATC AAGTTCGACA CTGGTAACCT GTGTATGGTG ACTGGAGGTG
       430        440        450        460        470        480
  CTAACCTAGG AAGAATTGGT GTGATCACCA ACAGAGAGAG GCACCCTGGA TCTTTTGACG
       490        500        510        520        530        540
  TGGTTCACGT GAAAGATGCC AATGGCAACA GCTTTGCCAC TCGACTTTCC AACATTTTTG
       550        560        570        580        590        600
  TTATTGGCAA GGGCAACAAA CCATGGATTT CTCTTCCCCG AGGAAAGGGT ATCCGCCTCA
       610        620        630        640        650        660
  CCATTGCTGA AGAGAGAGAC AAAAGACTGG CGGCCAAACA GAGCAGTGGG TGAAATGG
```

AvaII Fragment of clone 61

```
       250        260        270        280        290        300
      GATCTT TGTGGGCACA AAAGGAATCC CTCATCTGGT GACTCATGAT GCCCGCACCA
       310        320        330        340        350        360
  TCCGCTACCC CGATCCCCTC ATCAAGGTGA ATGATACCAT TCAGATTGAT TTAGAGACTG
       370        380        390        400        410        420
  GCAAGATTAC TGATTTCATC AAGTTCGACA CTGGTAACCT GTGTATGGTG ACTGGAGGTG
       430        440        450        460        470        480
  CTAACCTAGG AAGAATTGGT GTGATCACCA ACAGAGAGAG GCACCCTGGA TCTTTTGACG
       490        500        510        520        530        540
  TGGTTCACGT GAAAGATGCC AATGGCAACA GCTTTGCCAC TCGACTTTCC AACATTTTTG
       550        560        570        580        590        600
  TTATTGGCAA GGGCAACAAA CCATGGATTT CTCTTCCCCG AGGAAAGGGT ATCCGCCTCA
       610        620        630        640        650        660
  CCATTGCTGA AGAGAGAGAC AAAAGACTGG CGGCCAAACA GAGCAGTGGG TGAAATGGGT
       670
  CCCTGGTGAC ATGTCA.
```

BglII Fragment of clone 61

```
1
AA AAA ACA AAA CCA AAA CAT TCC GAA AAT GTC CAC AGC CTC ACG CCT ACC TGC CCT TAC

60              |AluI
CCT CAG CTC TTG GCT GGG TCT CCC ACT ATG CCC CAT CCC TCC TTC CCT CAG AGG CTG GGT
                                    met pro his pro ser phe pro gln arg leu gly
                                                      |AluI
120
GCC AGA GGG TGG ATG AGA AGA GAT TCT CAA AGC TGG GCA GGT CCC AGG AAA AGC CAC TTG
ala arg gly trp met arg arg asp ser gln ser trp ala gly pro arg lys ser his leu 180
ATC GAC CTG GGC AGT GAG GGG AAG CAG GGG GGT GGG AGG TGG TGG GGG
ile asp leu gly ser glu gly lys gln gly gly val gly gly arg trp trp gly 240
GAG CCA GAT GAG ATG TTC TCC GAC ATC TAC AAG ATC CGG GAG ATC GCG GAC GGG TTG TGC
glu pro asp glu met phe ser asp ile tyr lys ile arg glu ile ala asp gly leu cys
```

FIG. 15-2

```
300
CTG GAG GTG GAG GGG AAG ATG GTC AGT AGG ACA GAA GGT AAC ATT GAT GAC TCG CTC ATT
leu glu val glu gly lys met val ser arg thr glu gly asn ile asp asp ser leu ile ↓Kpn I
360
GGT GGA AAT GCC TCC GCT GAA GGC CCC GAG GGC GAA GGT ACC AGC ACA GTA ATC ACT
gly gly asn ala ser ala glu gly pro glu gly glu gly thr ser thr val ile thr 420
GGT GTC GAT ATT GTC ATG AAC CAT CAC CTG CAG GAA ACA GAA AGT TTC ACA AAA GAA TAC
gly val asp ile val met asn his his leu gln glu thr glu ser phe thr lys glu tyr 480
AAG AAG TAC ATC AAA GAT TAC ATG AAA TCA ATC AAA GGG AAA CTT GAA GAA CAG AGA CCA
lys lys tyr ile lys asp tyr met lys ser ile lys gly lys leu glu glu gln arg pro 540
GAA AGA GTA AAA CCT TTT ATG ACA GGG GCT GCA GAA CAA ATC AAG CAC ATC CTT GCT AAT
glu arg val lys pro phe met thr gly ala ala glu gln ile lys his ile leu ala asn
```

```
600
TTC AAA AAC TAC CAG TTC TTT ATT GGT GAA AAC ATG AAT CCA GAT GGC ATG GTT GCT CTA
phe lys asn tyr gln phe phe ile gly glu asn met asn pro asp gly met val ala leu 660
TTG GAC TAC CGT GAG GAT GGT GTG ACC CCA TAT ATG ATT TTC TTT AAG GAT GGT TTA GAA
leu asp tyr arg glu asp gly val thr pro tyr met ile phe phe lys asp gly leu glu 720
ATG GAA AAA TGT TAA CAA ATG TGG CAA TTA TTT TGG ATC TAT CAC CTG TCA TCA TAA CTG
met glu lys cys ***

780
GCT TCT GCT TGT CAT CCA CAC AAC ACC AGG ACT TAA GAC AAA TGG GAC TGA TGT CAT CTT

840
GAG CTC TTC ATT TAT TTT GAC TGT CTA AAA ATA AAA TGC ATT TAA ACT CAA AAA AAA AAA

900
ACA TGT CAT GTA GGT TGT CTA AAA ATA AAA TGC ATT TAA ACT CAA AAA ATA AAA AAA A
```

FIG. 15-3

```
5'.....AGCTTATGCTCTTGGCTGGGTCTCCCACTATGCCCCAT.....3'
3'.....ATACGAGAACCGACCCAGAGGGTGATACGGGGTA.....5'
```

| T4 DNA Polymerase
↓ dCTP

```
5'.....AGCTTATGCTCTTGGCTGGGTCTCCCACTATGCCCCAT.....3'
            CGAGAACCGACCCAGAGGGTGATACGGGGTA.....5'
```

| T4 DNA Polymerase
↓ dTTP

```
5'.....AGCTTATGCTCTTGGCTGGGTCTCCCACTATGCCCCAT.....3'
                                 TGATACGGGGTA.....5'
```

| S1 Nuclease
↓

```
                            ACTATGCCCCAT.....3'
                            TGATACGGGGTA.....5'
```

FIG. 18

HUMAN IL-2 LIKE POLYPEPTIDES, DNA SEQUENCES AND RECOMBINANT DNA MOLECULES THEREFORE AND METHODS FOR THE PRODUCTION AND USE THEREOF

This application is a continuation of U.S. Ser. No. 07/009,999 filed February 2, 1987, now abandoned, which is a continuation of U.S. Ser. No. 06/457,594 filed January 13, 1983, now abandoned, which is a continuation-in-part of U.S. Ser. No. 06/426,059 filed September 28, 1982, now abandoned.

IL-2 is a lymphokine with significant biological effects on a variety of T-lymphocyte activities. It is believed to be a product of helper T-cells and replaces these cells in cytotoxic responses. IL-2 is involved in concanavalin A (Con A) mediated mitogenesis of mouse thymocytes and in some instances can replace T-helper cells in antibody responses in vitro. It has T-cell growth factor (TCGF) activity and thus affords a powerful tool for examining cytotoxic T-cell activity at the clonal level. The ability of IL-2 to amplify cytotoxic responses makes it a very attractive candidate for specific tumor immunotherapy. IL-2 is also believed to play a mediator role in the production of immune interferon. The interaction of immune interefon with IL-2 is important in the induction of cytotoxic T-lymphocytes (CTL) (Farrar, W. L., et al., J. Immunol., 126, 1120 (1981)).

Human IL-2 is an antigen-nonspecific, genetically unrestricted soluble factor produced by erythrocyte rosette positive T-cells stimulated with antigens, mitogens and alloantigens. It is a protein with a reported molecular weight in the approximate range of 13,000 to 17,000 daltons (S. Gillis and J. Watson, J. Exp. Med., 152, 1709 (1980)) and an isoelectric point in the approximate range of pH 6–8. Human IL-2 has a number of in vitro and in vivo effects including the enhancement of the proliferative response of human peripheral blood mononuclear cells, or murine thymocytes, enhancement of the immune reponse in humans and in animals against bacterial, parasitic, fungal, protozoan and viral infections and the support of the growth of continuous T-cell lines.

Currently available methods for the production of human IL-2 involve stimulation of normal T-cells with an appropriate mitogen such as phytohaemagglutinin (PHA), or Con A, or a mitogen enhancing factor such as a combination of phorbol myristate acetate (PMA) and Con A. Since these T-cells require the presence of IL-2 for sustained growth in culture, the preparation of IL-2 is restricted to producing it batch-wise, thereby limiting the quantities of IL-2 produced and the time involved in the production. Furthermore, lymphokines including IL-2 are extremely difficult to purify. The presence of IL-2, therefore, has only been described in terms of its biological activity. IL-2 obtained by these methods has not been of sufficient purity to characterize the molecule in terms of its accurate molecular weight or its amino acid composition or sequence or to study its biological role and mechanism of action in detail.

In fact, there is some evidence to suggest that there may be different types of IL-2 produced by different types of T-cells or even that IL-2 might be but one component of a larger network or family of cell growth factors. Consequently, sufficient quantities of pure human IL-2 have not been available to carry out critical investigations of the extent and scope of the potential immunological and therapeutic uses of IL-2 and of the mechanism of action of gene regulation and cellular modulation of and by IL-2.

The synthesis of biologically active non-human IL-2, by translating mouse and gibbon ape m-RNA in *Xenopus laevis* oocytes, has been reported recently (Bleackley, R. C., et al., J. Biol Immunol., 127, 2432 (1981) and Lin, Y., et al., Biol. Chem., 257, 1587 (1982)).

Gillis, D. Mochizuki, P. J. Canlon, and S. H. Hefeneider, *Fed Proc Abstr*, 41(3), Abstract No. 1221 (1982), reported preparative biochemical separation schemes using SDS polyacrylamide gel electrophoresis for purification of human and murine interleukin-2.

D. Mochizuki and S. Gillis, *Fed Proc Abstr*, 41(3), Abstract No. 1222 (1982), developed an immune precipitation method using monoclonal anti-IL-2 antibodies to monitor human IL-2 gene expression.

S. Efrat, S. Pilo, and R. Kaempfer, *Nature*, 297 236 (1982), studied the kinetics of the appearance of mRNA for IL-2 and for IFN-γ in human lymphocytes stimulated by PHA using *Xenopus laevis* oocyte assay to measure IL-2 activity.

M. Okada, et al., Proc. Natl. Acad. Sci., 78, 1717–1721 (1981) established a human T-T hybridoma cell line which continuously secretes IL-2 or killer cell helper factor.

M. Rosenstein, et al., J. Immunol., 127, 566 (1981) reported that stimulated T-cells expanded in IL-2 are capable of mediating allogeneic skin graft rejections.

T. J. Eberlein, et al., J. Exp. Med., 156, 385 (1982) used long term T-cell lines to demonstrate the in vivo regression of established disseminated tumors.

SUMMARY OF THE INVENTION

The invention is directed to DNA sequences useful in isolating mRNA-encoding IL-2. These DNA sequences have the formula or complement to the formula:

| 10 | 20 | 30 | 40 | 50 | 60 |
|---|---|---|---|---|---|
| TCCTGAGGAA | CAGACTTAAG | TATGCCCTGA | CAGGAGATGA | AGTAAAGAAG | ATTTGCATGC |
| 70 | 80 | 90 | 100 | 110 | 120 |
| AGCGGTTCAT | TAAAATCGAT | GGCAAGGTCC | GAACTGATAT | AACCTACCCT | GCTGGATTCA |
| 130 | 140 | 150 | 160 | 170 | 180 |
| TGGATGTCAT | CAGCATTGAC | AAGACGGGAG | AGAATTTCCG | TCTGATCTAT | GACACCAAGG |
| 190 | 200 | 210 | 220 | 230 | 240 |
| GTCGCTTTGC | TGTACATCGT | ATTACACCTG | AGGAGGCCAA | GTACAAGTTG | TGCAAAGTGA |
| 250 | 260 | 270 | 280 | 290 | 300 |
| GAAAGATCTT | TGTGGGCACA | AAAGGAATCC | CTCATCTGGT | GACTCATGAT | GCCCGCACCA |
| 310 | 320 | 330 | 340 | 350 | 360 |
| TCCGCTACCC | CGATCCCCTC | ATCAAGGTGA | ATGATACCAT | TCAGATTGAT | TTAGAGACTG |
| 370 | 380 | 390 | 400 | 410 | 420 |
| GCAAGATTAC | TGATTTCATC | AAGTTCGACA | CTGGTAACCT | GTGTATGGTG | ACTGGAGGTG |
| 430 | 440 | 450 | 460 | 470 | 480 |
| CTAACCTAGG | AAGAATTGGT | GTGATCACCA | ACAGAGAGAG | GCACCCTGGA | TCTTTTGACG |
| 490 | 500 | 510 | 520 | 530 | 540 |

| | | | | | |
|---|---|---|---|---|---|
| TGGTTCACGT | GAAAGATGCC | AATGGCAACA | GCTTTGCCAC | TCGACTTTCC | AACATTTTTG |
| 550 | 560 | 570 | 580 | 590 | 600 |
| TTATTGGCAA | GGGCAACAAA | CCATGGATTT | CTCTTCCCCG | AGGAAAGGGT | ATCCGCCTCA |
| 610 | 620 | 630 | 640 | 650 | 660 |
| CCATTGCTGA | AGAGAGAGG | AAAAGACTGG | CGGCCAAACA | GAGCAGTGGG | TGAAATGGGT |
| 670 | 680 | 690 | 700 | 710 | 720 |
| CCCTGGTGAC | ATGTCAGATC | TTTGTACGTA | ATTAAAAATA | TTGTGGCAGG | ATTAATAGC | or

| | | | | | |
|---|---|---|---|---|---|
| | | 10 | 20 | 30 | 40 | 50 | 60 |
| AAAAAACAAA | ACCAAAACAT | TCCGAAAATG | TCCACAGCCT | CACGCCTACC | TGCCCTTACC |
| 70 | 80 | 90 | 100 | 110 | 120 |
| CTCAGCTCTT | GGCTGGGTCT | CCCACTATGC | CCCATCCCTC | CTTCCCTCAG | AGGCTGGGTG |
| 130 | 140 | 150 | 160 | 170 | 180 |
| CCAGAGGGTG | GATGAGAAGA | GATTCTCAAA | GCTGGGCAGG | TCCCAGGAAA | AGCCACTTGA |
| 190 | 200 | 210 | 220 | 230 | 240 |
| TCGACCTGGG | CAGTGAGGGG | AAGCAGGGGG | TGGGGGGTGG | GGTGGGGAGG | TGGTGGGGGG |
| 250 | 260 | 270 | 280 | 290 | 300 |
| AGCCAGATGA | GATGTTCTCC | GACATCTACA | AGATCCGGGA | GATCGCGGAC | GGGTTGTGCC |
| 310 | 320 | 330 | 340 | 350 | 360 |
| TGGAGGTGGA | GGGGAAGATG | GTCAGTAGGA | CAGAAGGTAA | CATTGATGAC | TCGCTCATTG |
| 370 | 380 | 390 | 400 | 410 | 420 |
| GTGGAAATGC | CTCCGCTGAA | GGCCCCGAGG | GCGAAGGTAC | CGAAAGCACA | GTAATCACTG |
| 430 | 440 | 450 | 460 | 470 | 480 |
| GTGTCGATAT | TGTCATGAAC | CATCACCTGC | AGGAAACAAG | TTTCACAAAA | GAAGCCTACA |
| 490 | 500 | 510 | 520 | 530 | 540 |
| AGAAGTACAT | CAAAGATTAC | ATGAAATCAA | TCAAAGGGAA | ACTTGAAGAA | CAGAGACCAG |
| 550 | 560 | 570 | 580 | 590 | 600 |
| AAAGAGTAAA | ACCTTTTATG | ACAGGGGCTG | CAGAACAAAT | CAAGCACATC | CTTGCTAATT |
| 610 | 620 | 630 | 640 | 650 | 660 |
| TCAAAAACTA | CCAGTTCTTT | ATTGGTGAAA | ACATGAATCC | AGATGGCATG | GTTGCTCTAT |
| 670 | 680 | 690 | 700 | 710 | 720 |
| TGGACTACCG | TGAGGATGGT | GTGACCCCAT | ATATGATTTT | CTTTAAGGAT | GGTTTAGAAA |
| 730 | 740 | 750 | 760 | 770 | 780 |
| TGGAAAAATG | TTAACAAATG | TGGCAATTAT | TTTGGATCTA | TCACCTGTCA | TCATAACTGG |
| 790 | 800 | 810 | 820 | 830 | 840 |
| CTTCTGCTTG | TCATCCACAC | AACACCAGGA | CTTAAGACAA | ATGGGACTGA | TGTCATCTTG |
| 850 | 860 | 870 | 880 | 890 | 900 |
| AGCTCTTCAT | TTATTTTGAC | TGTGATTTAT | TTGGAGTGGA | GGCATTGTTT | TTAAGAAAAA |
| 910 | 920 | 930 | 940 | | |
| CATGTCATGT | AGGTTGTCTA | AAAATAAAAT | GCATTTAAAC TC | | | or

| | | | | | |
|---|---|---|---|---|---|
| 310 | 320 | 330 | 340 | 350 | 360 |
| A | GGGGAAGATG | GTCAGTAGGA | CAGAAGGTAA | CATTGATGAC | TCGCTCATTG |
| 370 | 380 | 390 | 400 | 410 | 420 |
| GTGGAAATGC | CTCCGCTGAA | GGCCCCGAGG | GCGAAGGTAC | CGAAAGCACA | GTAATCACTG |
| 430 | 440 | 450 | 460 | 470 | 480 |
| GTGTCGATAT | TGTCATGAAC | CATCACCTGC | AGGAAACAAG | TTTCACAAAA | GAAGCCTACA |
| 490 | 500 | 510 | 520 | 530 | 540 |
| AGAAGTACAT | CAAAGATTAC | ATGAAATCAA | TCAAAGGGAA | ACTTGAAGAA | CAGAGACCAG |
| 550 | 560 | 570 | 580 | 590 | 600 |
| AAAGAGTAAA | ACCTTTTATG | ACAGGGGCTG | CAGAACAAAT | CAAGCACATC | CTTGCTAATT |
| 610 | 620 | 630 | 640 | 650 | 660 |
| TCAAAAACTA | CCAGTTCTTT | ATTGGTGAAA | ACATGAATCC | AGATGGCATG | GTTGCTCTAT |
| 670 | 680 | 690 | 700 | 710 | 720 |
| TGGACTACCG | TGAGGATGGT | GTGACCCCAT | ATATGATTTT | CTTTAAGGAT | GGTTTAGAAA |
| 730 | 740 | 750 | 760 | 770 | 780 |
| TGGAAAAATG | TTAACAAATG | TGGCAATTAT | TTTGGATCTA | TCACCTGTCA | TCATAACTGG |
| 790 | 800 | 810 | 820 | 830 | 840 |
| CTTCTGCTTG | TCATCCACAC | AACACCAGGA | CTTAAGACAA | ATGGGACTGA | TGTCATCTTG |
| 850 | 860 | 870 | 880 | 890 | 900 |
| AGCTCTTCAT | TTATTTTGAC | TGTGATTTAT | TTGGAGTGGA | GGCATTGTTT | TTAAGAAAAA |
| 910 | 920 | 930 | 940 | | |
| CATGTCATGT | AGGTTGTCTA | AAAATAAAAT | GCATTTAAAC TC | | |

The IL-2 encoded by the RNA prepared in accordance with this invention is useful in the diagnosis and treatment of human and animal cancer, tumors of various types, viral, bacterial, fungal, parasitic and protozoan infections, immune deficiencies and in a variety of other therapeutic and diagnostic applications where the administration of IL-2 is indicated.

This invention is also directed to methods for producing cDNA of the invention and of producing IL-2 in an oocyte translation system. The cDNA sequences of the invention are also useful as probes in obtaining the relevant IL-2 encoding sequence from the genome.

BRIEF DESCRIPTION OF THE DRAWINGS

FIG. 4 shows the nucleotide sequence of clone 61 along with the corresponding amino acid sequence.

FIG. 5 shows the nucleotide sequences of the AvaII and BglII fragments of clone 61.

FIG. 15 represents a nucleotide sequence of clone 34 containing the ATG initiation codon, along with the corresponding amino acid sequence.

FIG. 18 is a schematic representation of the enzymatic degradation of clone pSY2601 to remove part of the nucleotide segment shown in FIG. 17.

DESCRIPTION OF THE INVENTION

Figure 1:
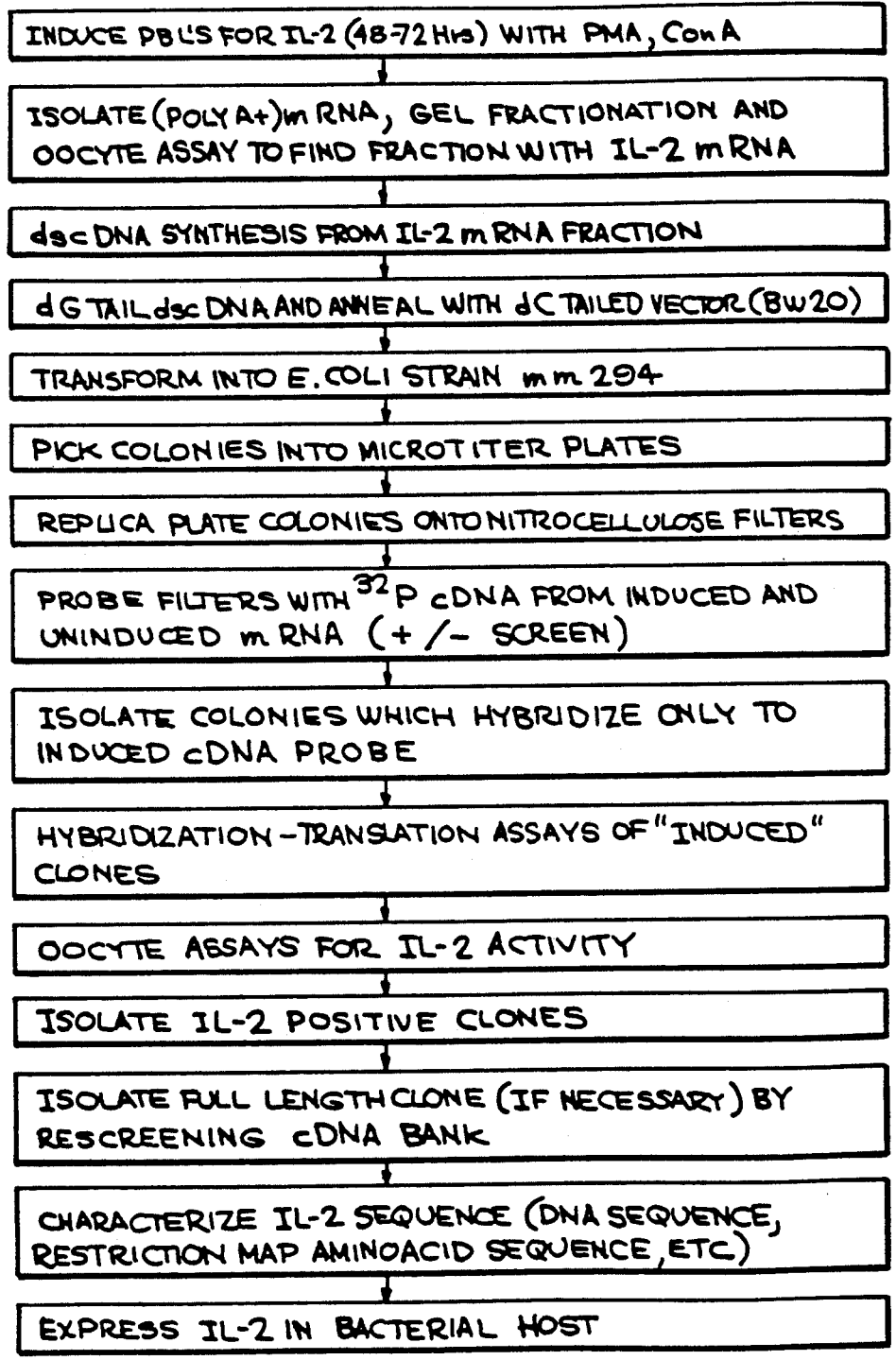
FIG. 1 is a schematic representation of a proposed process to isolate and identify the human IL-2 gene.
Figure 2:
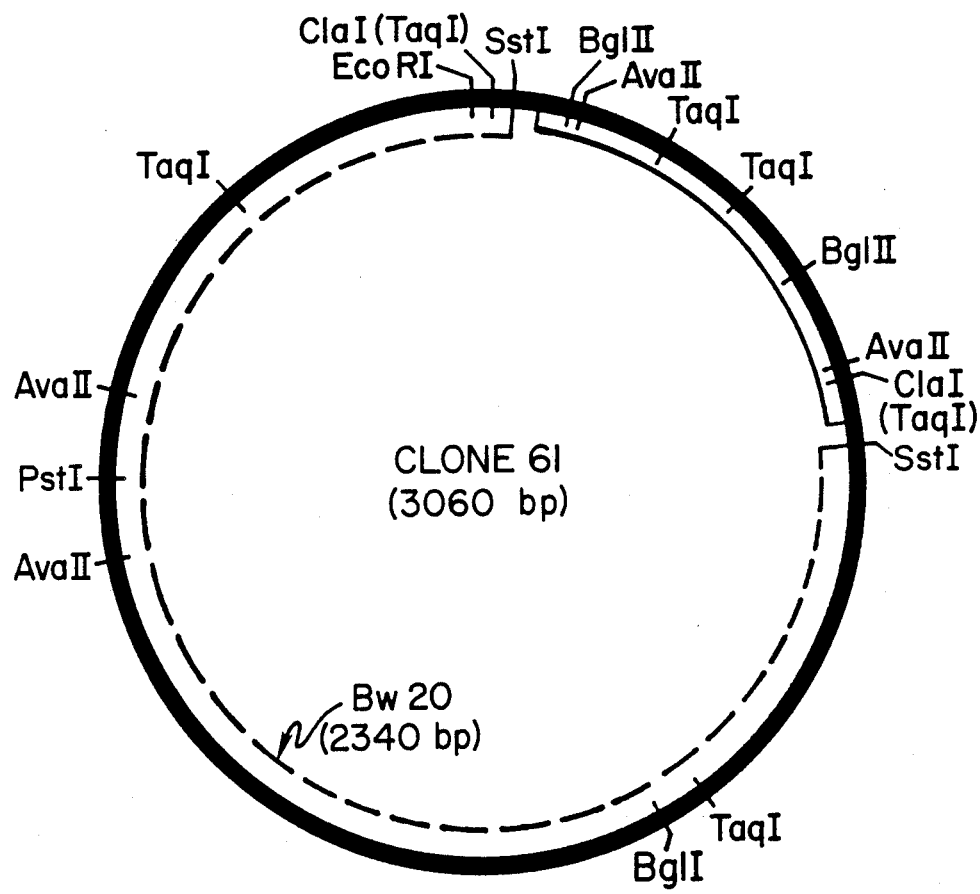
FIG. 2 is a diagram of clone 61.

FIG. 1 shows the steps involved in the process usable in the isolation and characterization of the human IL-2 gene through the expression of the gene in a bacterial host, in accordance with the present invention.

The sequence of the steps include inducing PBLs for IL-2 production by treatment with a combination of PMA and Con A for 48 to 72 hours; isolating and characterizing polyA containing mRNA by separation techniques known in the art (such as by gel fractionation); microinjecting the mRNA into *Xenopus laevis* oocytes and assaying for resulting IL-2 activity; synthesizing double stranded complementary DNA (ds-cDNA) using the IL-2 mRNA as a template; adding dG tails to the ds-cDNA and annealing into the dC tailed SstI site of a vector such as pBW20 which is a derivative of pBR322 to generate a recombinant DNA molecule; transforming a suitable bacterial host such as strain MM294 of *E. coli* with the recombinant DNA (rDNA) molecule; picking colonies of transformants onto microtiter plates; replica plating colonies onto nitrocellulose filters; after denaturing the DNA, probing the transformant DNA with $^{32}$p labeled cDNA from induced and uninduced mRNA (+/−screening); isolating colonies which hybridize only to induced cDNA probe; assaying by hybridization-translation of "induced" clones; checking for IL-2 activity by oocyte assays and isolating IL-2 positive clones; rescreening the cDNA bank to isolate full length clones if found to be necessary by DNA sequencing; determining the DNA sequences, restriction maps of the clones. The individual steps involved are described in greater experimental detail in the examples provided.

Human IL-2 mRNA can be obtained from T-lymphocytes that have been induced for IL-2 production with antigens, mitogens and alloantigens. PBLs, spleen cells, thoracic duct cells, lymph node cells, bone marrow cells, and tonsil cells are exemplary sources of T lymphocytes. PBLs are more conveniently used rather than tissue cells. PBLs are usually separated from whole blood by density gradient centrifugation. This involves layering the blood over a gradient medium of appropriate specific gravity. The most suitable gradient media for separating lymphocytes from red cells and granulocytes are high molecular weight polymers, preferably cross-linked polymers including but not limited to cross-linked epichlorohydrin-sucrose polymer (Ficoll), or diatrizoate polymers such as 3,5-diacetamido-2,3,6-tri-iodobenzoic acid sodium salt (Hypaque), Ficoll-Hypaque and Lymphoprep. The layered blood is centrifuged using a low centrifugal field, usually about $300 \times g$ for about 20–30 minutes, to prevent disruption of the cell membrane. The lymphocytes form a band in a gradient medium while the red cells and granulocytes pass through. The blood cells are usually suspended in a balanced salt solution for centrifugation. Following gradient centrifugation, the PBLs are harvested from the interface and washed to remove residual gradient medium.

The PBLs are then cultured in an appropriate growth medium, such as Dulbecco's Modified Eagle's Medium (DME) (Moore, G. E., et al., J. Natl. Cancer Inst., 36, 405 (1966)) and the like, containing an inducer such as PHA, PMA, Con A and mixtures thereof, enzymes such as neuraminidase and galactose oxidase, and other antigens or mitogens, to induce the production of IL-2. The concentration of the inducer used in the medium depends upon the particular inducer and the cell concentration. The cell concentration is usually in the range of about $1 \times 10^6$/ml to $6 \times 10^6$/ml and the concentration of the inducer is usually in the range of about 1 ng to about 10 micrograms depending on the inducer of choice. For example, when PMA is used in the induction protocol, its concentration is usually in the range of about 1 to 5 ng/ml and that of Con A is about 5 to 10 micrograms/ml; when PHA is used as the inducer, its concentrations are in the 0.8 to 2.0 µg/ml range. The cells are incubated in the inducer-containing medium, typically for about 1 to 3 days.

Following the incubation, the cells are harvested and the total cytoplasmic RNA is isolated, preferably under conditions where the degradation of mRNA is prevented. The isolation is usually accomplished by lysing the cells, removing nuclei from the lysate by centrifugation, extracting the supernatant with a suitable organic extractant including but not limited to phenol-chloroform mixtures, and precipitating the RNA from the extract with alcohols such as ethanol. The total cytoplasmic RNA is enriched in poly-adenylated mRNA by means of column chromatography utilizing packing materials containing oligo dT, poly U or other molecules which exhibit a base-pairing affinity for poly A, thereby separating mRNA from other types of RNA (such as ribosomal and transfer RNA).

IL-2 mRNA is identified by resolving the total mRNA isolated into different molecular weight or size fractions, translating each of the fractions in *Xenopus laevis* oocytes and assaying the oocyte lysate of each fraction for IL-2 activity as described in Example 2, infra. The fractionation of the total mRNA can be accomplished by methods known in the art, including but not limited to gel electrophoresis, gradient centrifugation, chromatography and the like. Size estimates of the fractions are usually made by comparison with known RNA markers run in parallel fractionations. Aliquots of each fraction are microinjected into *Xenopus laevis* oocytes. The oocytes are incubated for about 48 hours after the injection. The supernatant and the lysates of the oocytes are assayed for IL-2 activity by the methods described in Gillis, S., et al., (J. Immunol. 120, 2027-2032 (1978). IL-2 activity occurs in PBL mRNA at about 1.0 to about 1.2 kb.

The 1.0 to 1.2 kb mRNA fractionate exhibiting IL-2 activity in the oocyte assay is used to synthesize ds-cDNA by oligo dT priming and reverse transcription. The resulting cDNA is cloned in an appropriate animal or bacterial host, usually E. coli, by the oligo dG/oligo dC tailing method using an appropriate cloning vector such as, for example, pBR322, variants and modificants thereof.

Single stranded $^{32}$p cDNA hybridization probes are prepared using as templates uninduced PBL mRNA and the 1.0-1.2 kb mRNA exhibiting IL-2 activity in the oocyte assay. The reverse transcription and labeling of these mRNAs is usually carried out by methods known in the art using oligo dT to prime the synthesis.

The cDNA clones made from the IL-2 active mRNA fractions are screened by hybridizing them with the radiolabelled single stranded cDNA probes derived from the uninduced and the induced PBL mRNA as described above. By this "plus-minus" screening of the cDNA bank, clones containing nucleotide sequences not present in the mRNA population of uninduced PBLs are isolated.

Induction specific cDNA clones are screened by hybridization selection using induced PBL mRNA. IL-2 clones are identified by their ability to enrich for mRNA that translates in oocytes to give IL-2 activity. IL-2 clones are characterized by using restriction enzymes and sequencing the cDNA insert. The cDNA library is rescreened by hybridization to a radiolabelled probe made from the IL-2 cDNA insert and the positive clones are characterized as described above.

The cDNA clones are screened by hybridization-translation using oocyte IL-2 assay which involves hybridization selection of induced PBL mRNA, translation of the selected mRNA in *Xenopus* oocytes and assay of the product for IL-2 biological activity.

The IL-2 positive clones are utilized to rescreen the cDNA bank to isolate full length clones, if the DNA sequences indicate the necessity for obtaining full length clones. At least two full length clones, designated as clones 61 and 34 were isolated and used for rescreening the cDNA and the genomic banks. Several other clones isolated and tested were substantially identical to either clone 61 or 34 or were smaller fragments thereof.

The IL-2 positive clones, fragments or derivatives thereof are also used, in turn, as probes to screen the genomic library.

The total human genomic DNA is then screened by digesting it with various restriction enzymes and using the Southern blotting technique to identify the various restriction fragments. Similarity of restriction patterns indicates if an individual clone isolated by the preceding steps is part of a family of related genes.

Assembly of a plasmid or other transforming vector for the direct expression of the human IL-2 gene or genes in an appropriate host, preferably E. coli, involves operatively linking to or splicing into the transforming vector containing the gene or gene fragment, an appropriate expression control sequence comprising a promoter, operator and leader ribosome binding site, just preceding the ATG initiation codon for human IL-2. Promoter systems commonly used in the expression control are trp, lac, B-lac, major operator and promoter region of phage $\gamma$, the control region of fd coat protein and other similar sequences which control expression of genes in eukaryotic and prokaryotic cells and their viruses.

The following examples are presented to help in the better understanding of the subject invention and for illustrative purposes only. They are not to be construed as limiting the scope of the invention in any manner or means.

EXAMPLE 1

Isolation of Messenger RNA (mRNA)

Human PBLs were purified from buffy coats by centrifugation on Ficoll-Hypaque (A. Boyum, Scand. J. Clin. Invest., 21: Suppl. 97: 77 (1968)). The cells were then incubated in DM with 10% fetal calf serum to a concentration of $4 \times 10^6$ cells/ml and induced for IL-2 production with the addition of phorbol myristate acetate (5 ng/ml) and concanavalin A (10 $\mu$g/ml) as described by J. J. Farrar and J. Fuller-Farrar, Prog. Cancer Res. Therapy, 20: 49-55 (1981) and B. M. Stadler, et al., J. Immunol., 127 1936 (1981). The cells were harvested at 48 or 72 hours. Total cytoplasmic ribonucleic acid (RNA) was isolated from the induced cells by the following protocol: all steps were at 4° C. Cells were washed twice in PBS (phosphate buffered saline) and resuspended in IHB (140 mM NaCl, 10 mM Tris, 1.5 mM MgCl, pH 8) containing 10 mM vanadyl adenosine complex (S. L. Berger and C. S. Birkenmeier, Biochem., 18, 5143 (1979)).

A non-ionic detergent of the ethylene oxide polymer type (NP-40) was added to 0.3% to lyse the cellular, but not nuclear, membranes. Nuclei were removed by centrifugation at 1,000$\times$g for 10 minutes. The post-nuclear supernatant was added to an equal volume of TE (10 mM Tris, 1 mM EDTA, pH 7.5) saturated phenol chloroform (1:1) containing 0.5% SDS and 10 mM EDTA. The supernatant was re-extracted 4 times and phase separated by centrifugation at 2000$\times$g for 10 minutes. The RNA was precipitated by adjusting the sample to 0.25 M NaCl, adding 2 volumes of 100% EtOH and storing at $-20°$ C. The RNA was pelleted at 5,000$\times$g for 30 minutes, washed with 70% and 100% ethanol, then dried. Polyadenylated (Poly A+) messenger RNA (mRNA) was obtained from the total cytoplasmic RNA by chromatography on oligo dT cellulose (J. Aviv and P. Leder, Proc. Natl. Acad. Sci., 69, 1408-1412 (1972)). The RNA was dissolved in ETS (10 mM Tris, 1 mM EDTA, 0.5% SDS, pH 7.5) at a concentration of <2 mg/ml. This solution was heated to 65° C. for 5 minutes, then quickly chilled to 4° C. After bringing the RNA solution to room temperature, it was adjusted to 0.4M NaCl and slowly passed through an oligo dT cellulose column previously equilibrated with binding buffer (500 mM NaCl, 10 mM Tris, 1 mM EDTA, pH 7.5). The flow-through was passed over the column twice more. The column was then washed with 10 volumes of binding buffer. Poly A+mRNA was eluted with aliquots of ETS, extracted once with TE-saturated phenol chloroform and precipitated by the addition of NaCl to 0.2M and 2 volumes of 100% ethanol. The RNA was re-precipitated twice, washed once in 70% and then in 100% ethanol prior to drying.

EXAMPLE 2

Fractionation and Analysis of mRNA

The PBL poly A+ mRNA was fractionated by preparative agarose slab gel electrophoresis under fully denaturing conditions using 10 mM methyl mercury (CH₃HgOH) as the denaturant (J. M. Bailey and N. Davidson, Anal. Biochem. 70:75-85 (1976); and P. B. Sehgal and A. D. Sagar, Nature 288:95-97 (1980)). 1.5% gels were prepared by melting agarose in running buffer (100 mM boric acid, 6 mM sodium borate, 10 mM sodium sulfate, 1 mM EDTA, pH 8.2), cooling to 60° C. and adding 1/100 volume of 1M CH₃HgOH. 6 mm slab gels were used for preparative electrophoresis. Poly A+ RNA was dissolved in 0.5×running buffer and denatured by incubation in 10 mM methyl mercury for 10 minutes at room temperature. Glycerol (20%) and bromophenol blue (0.05%) were added for loading the samples. Samples were electrophoresed for 500-600 volt hours with recirculation of the buffer. After electrophoresis, the gel was washed for 40 minutes in 100 mM 2-mercaptoethanol to detoxify the methyl mercury. The preparative sample lanes were sliced out and the lanes containing molecular weight RNA size markers were stained with 0.5 μg/ml ethidium bromide, destained and photographed. The sample lanes were cut into 3 mm sections. Each section was placed in a 1.5 ml Eppendorf microfuge tube containing 3 volumes of NETS (100 mM NaCl, 10 mM Tris, 10 mM EDTA, 0.2% SDS, pH 7.5) and 10 μg E. coli tRNA. The tubes were then incubated at 95° C. for 5 minutes to melt the agarose, quick frozen and immediately spun, full-speed, in a microcentrifuge for 10-15 minutes at room temperature. The supernatants were removed and extracted 2×with TE-saturated phenol-chloroform. RNA was precipitated by addition of sodium acetate, pH 5, to 0.2M and 2.5 volumes of 100% ethanol. The RNA was reprecipitated, washed with 70% and 100% ethanol, dried and dissolved in water.

To determine the location of IL-2 mRNA sequences in the gel fractions, aliquots of RNA from each fraction were injected into *Xenopus laevis* oocytes and the oocyte lysates assayed for IL-2 activity on HT-2 cells, (J. Watson, J. Exp. Med., 150:1510-1519 (1979) and S. Gillis, et al., J. Immunol. 120, 2027-2032 (1978)). Four days before use, the *Xenopus laevis* amphibians were injected with 100 units of Gestyl (pregnant mare serum gonadotropin). The ovaries were removed surgically and individual, stage V-VI, oocytes isolated and placed in Barth's medium (J. N. Dumont, J. Morphol., 136: 153-164 (1972) and J. B. Gordon, J. Embryol. Exp. Morphol., 20: 401-414 (1968)). The oocytes were injected with 50 nl of mRNA (1-3 mg/ml in water) and incubated in Barth's medium (10 μl/oocyte containing 0.1 mM PMSF (phenyl methyl sulfonyl fluoride) and 1×Penicillin-Streptomycin-Fungizone solution for 36 hours at 21° C. The oocytes were homogenized in the media used for incubation. Debris was pelleted by centrifugation for 10 minutes in a microcentrifuge and the supernatant removed for measurement of biological activity in the IL-2 assay. An IL-2 activity peak was found at approximately 1.0-1.2 kb. Complementary DNA (cDNA) clones were obtained from these fractions as described in the next section.

EXAMPLE 3

Construction of Complementary DNA (cDNA)

cDNA was made to the PBL mRNA fraction that contained IL-2 activity (as determined by the oocyte IL-2 assay), using oligo dT priming of the poly A tails and AMV reverse transcriptase (M. P. Wickens, et al., J. Biol. Chem. 253: 2483-2495 (1978)). The mRNA sample was denatured by treatment with 10 mM methyl mercury at 22° C. for 5 minutes and detoxified by the addition of 100 mM 2-mercaptoethanol (F. Payvar and R. T. Schimke, J. Biol. Chem. 254: 7636-7642 (1979)). First strand cDNA synthesis reaction was carried out in 50 mM Tris pH 8.0, 50 mM KCl, 6 mM MgCl₂, 20 mM 2-mercaptoethanol, 1 mM dATP, 1 mM dGTP, 1 mM dCTP, 1 mM dTTP, 1000 U/ml RNasin, 20 μg/ml oligo dT, and 50 units of reverse transcriptase at 42° C. for 1 hour. The reaction was stopped and the RNA hydrolyzed by adjusting the sample to 0.25M NaOH and heating at 45° C. for 30 minutes. The sample was neutralized with HCl and extracted with a phenol-CHCl₃ mixture. The cDNA product was purified by multiple ethanol precipitations, washed with 70% ethanol, 100% ethanol, and dried.

The second-strand was synthesized with reverse transcriptase utilizing the 5' snap-back structure of the first strand as primer by the method of T. Maniatis, E. F. Fritsch and J. Sambrook, "Molecular Cloning: A Laboratory Manual." Cold Spring Harbor Laboratory. 236 (1982). First-strand cDNA pellet was dissolved in reaction buffer (see above) without RNasin and oligo dT. Fifty units of reverse transcriptase were added and the sample was incubated at 42° C. for 2 hours. The reaction was stopped by adjusting the solution to 25 mM EDTA, 0.5% SDS and heating at 65° C. for 5 minutes. The sample was ethanol precipitated and resuspended in S₁ nuclease buffer (200 mM NaCl, 30 mM NaOAc pH 4.6, and 2 mM ZnSO₄). The double stranded cDNA product was digested with S₁ nuclease at 25° C. for 20 minutes to give blunt ends by opening up the hairpin loop structures and destroying single-strand branches in the DNA. (A. Efstratiadis and L. Villa-Komaroff (1979). "Cloning of Double Stranded DNA." Genetic-Engineering Ed. J. K. Setlow and A. Hollaender, vol. 1, p. 15, Plenum Press, N. Y.) The sample was placed on ice and adjusted to 25 mM EDTA and 0.5% SDS. The double-stranded cDNA product was extracted with phenol-CHCl₃ and ethanol precipitated.

Poly dG tails were added to the 3' end of the cDNA product using terminal transferase. (Guo-ren Deng and R. Wu, Nuc. Acids Res. 9: 4173-4188 (1981)). The double stranded cDNA product was dissolved in 100 mM potassium cacodylate pH 7.0, 1 mM CoCl₂, 1 mM MnCl₂, 0.2 mM DTT, 20 mM dGTP and terminal transferase. The reaction was incubated at 30° C. for 60 minutes and stopped by adjusting to 25 mM EDTA and 0.5% SDS. The sample was extracted with phenol-CHCl₃ and ethanol precipitated.

The plasmid pBW20, a derivative of pBR322 which contains a single SstI restriction site and confers ampicilling (Amp) resistance, was the vector used in cloning the IL-2 cDNA. This vector was digested with SstI and the linear form isolated on agarose gel. The pBW20 linear form was tailed with poly dC using terminal transferase according to the procedure described above.

EXAMPLE 4

Transformation and Isolation of Recombinant Clones

The dG tailed cDNA was annealed to dC tailed pBW20 plasmid in 100 mM NaCl, 10 mM Tris, pH 7.5, and 2 mM EDTA by heating at 65° C. for 3 minutes, incubating at 42° C. for 2 hours, and slow cooling to 22° C. (W. Rowekamp and R. A. Firtel, Dev. Biol. 79: 409 (1980)). Competent MM294 cells, derivatives of E. coli K12, were transformed by the addition of the annealed DNA. Cells were incubated at 0° C. for 30 minutes, heat shocked at 37° C. for 5 minutes, and then incubated in L broth at 37° C. for 60 minutes. (T. Maniatis, E. F. Fritsch and J. Sambrook (1982) "Molecular Cloning: A Laboratory Manual." Cold Spring Harbor Laboratory. p. 249). Cells were plated on L agar plates containing 50 μg/ml Amp and the transformants were allowed to grow at 37° C. for 15 hours. Drug resistant clones were picked into 96 well microtiter plates and grown in L broth containing 50 μg/ml Amp.

EXAMPLE 5

Screening and Identification of IL-2 cDNA Clones

The IL-2 cDNA library was screened using the colony hybridization procedure. Each microtiter plate was replicated onto duplicate nitrocellulose filter papers (S & S type BA-85) and colonies were allowed to grow at 37° C. for 14–16 hours on L-agar containing 50 μg/ml Amp. The colonies were lysed and DNA fixed to the filter by sequential treatment for 5 minutes with 500 mM NaOH, 1.5M NaCl, washed twice for 5 minutes each time with 5×standard saline citrate (SSC). Filters were air dried and baked at 80° C. for 2 hours. The duplicate filters were prehybridized at 42° C. for 6–8 hours with 10 ml per filter of DNA hybridization buffer (50% formamide, 5×SSC, pH 7.0 5×Denhardt's solution (polyvinylpyrrolidine, plus ficoll and bovine serum albumin; 1×=0.02% of each), 50 mM sodium phosphate buffer at pH 7.0, 0.2% SDS, 20 μg/ml Poly U, and 50 μg/ml denatured salmon sperm DNA). $^{32}$p labelled cDNA probes were prepared from induced PBL mRNA (IL-2 mRNA fraction) or uninduced PBL mRNA using oligo dT priming and reverse transcriptase as described for first strand cDNA synthesis except $^{32}$p dCTP was used. One set of filters was hybridized to $5\times10^5$ cpm/ml of induced and the other set was hybridized to $5\times10^5$ cpm/ml of uninduced $^{32}$p cDNA probe. The samples were hybridized at 42° C. for 24–36 hours with 5 ml/filter of DNA hybridization buffer containing the appropriate $^{32}$p cDNA probe. The filters were washed four times for 30 minutes each time at 37° C. with 2×SSC, 0.2% SDS and 50 mM sodium phosphate buffer at pH 7, then washed twice with 2×SSC and 0.2% SDS, air dried, and autoradiographed at −70° C. for 2 to 3 days.

1750 recombinant clones were screened by colony hybridization using $^{32}$p cDNA probes made from induced or uninduced human PBL mRNA. (M. Grunstein and D. Hogness, Proc. Natl. Acad. Sci. 72: 3961 (1975)). Approximately 380 of the clones hybridized to the induced probe and showed very little hybridization to the uninduced probe. The recombinant plasmids contained in the induction-specific clones were analyzed using a miniprep restriction procedure to determine the size and relationship of the cDNA inserts (D. Ish-Horowicz and J. F. Burke, Nuc. Acids Res. 9: 2989–2998. (1981)). Plasmid DNA was purified from 280 of the clones that contained cDNA inserts greater than 200 base pairs in size, using a lysozyme-Triton lysis procedure and CsCl-ethidium bromide banding of the supercoil DNA.

cDNA clones were screened by the hybridization-translation oocyte IL-2 assay which involves hybridization selection of induced PBL mRNA by separation techniques known in the art, translation of the eluted mRNA in oocytes and assay of the product for IL-2 biological activity. 20 μg of each cDNA clone was analyzed as a pool of 4 or 5 clones. The plasmid DNA was denatured and subjected to limited hydrolysis by heating at 100° C. for 15 minutes in 0.2N NaOH. The DNA samples were adjusted to 1.1M NH4OAc by the addition of 9 volumes of cold 1.2M NH4OAc and bound to type HA nitrocellulose filters by multiple cycles ("Triton" is a tradename for a detergent preparation.) of slow filtration. The filters were then washed with 6×SSC, air dried, and heated at 80° C. for 2 hours in a vacuum oven to fix the DNA. (F. C. Kafatos, et al., Nuc. Acids Res. 7: 1541–1552 (1979)).

The filters were prehybridized in 1 ml hybridization-selection buffer (50% formamide, 20 mM Pipes pH 7.5, 800 mM NaCl, 1 mM EDTA, and 0.2% SDS) containing 200 μg/ml E. coli tRNA at 37° C. for 6 hours. The prehybridization mix was removed and 0.5 ml fresh hybridization buffer was added which contained 40 μg/ml of induced human PBL mRNA that had previously shown high levels of IL-2 activity in the oocyte IL-2 assay. The hybridization reaction mixtures were incubated at 37° C. for 14–16 hours. The hybridization mixture was removed and the unbound RNA was ethanol precipitated and processed as described below for the eluted RNA samples.

The filters were washed twice at 37° C. with 1 ml of fresh hybridization buffer, followed by 3 washes with 50 ml of 2 ×SSC, and 0.1% SDS, and then 3 times with 50 ml of 0.1×SSC and 0.1% SDS. The hybridized RNA was eluted from the filters in a sterile, siliconized vial containing 0.5 ml of elution buffer (5 mM EDTA, 10 μg/ml E. coli rRNA) at 90° C. for 3 minutes. (M. McGrogan, et. al., Nuc. 'Acids Res. 6(2):593–607 (1979)). The eluted RNA was adjusted to 250 mM NaCl, 0.2% SDS, and extracted with phenol-CHCl3. The RNA was ethanol precipitated, reprecipitated, washed with 70% ethanol, 100% ethanol, and dried under vacuum. The hybridized-selected RNA samples were dissolved at a concentration of 1 mg/ml carrier tRNA and treated as described by injection into oocytes and measurement of IL-2 activity in the biological assay.

Pooled clones that were found to be positive in the IL-2 assay were then analyzed as individual samples in the hybridization-translation assay. The IL-2 cDNA clones that were identified by this assay were characterized using standard restriction enzyme technology and a partial restriction map constructed. The cDNA insert was then sequenced using the Maxam-Gilbert procedure (A. Maxam and W. Gilbert in "Methods in Enzymology." 65(1): 497–559 (1980)) and the sequence of the protein was deduced from the DNA sequence.

Six clones, designated as clones 54, 61, 96, 141, 34 and 111 were isolated. Clones 54, 61, 96 and 141 exhibited almost identical nucleotide sequences and partial or complete sequence homology with a number of other genomic clones, indicating the existence of a family of related genes. Clone 96 differs from clone 61 in one nucleotide at base position 353, from TTA to TTG, which does not, however, result in a change in the corresponding amino acid.

Figure 3:
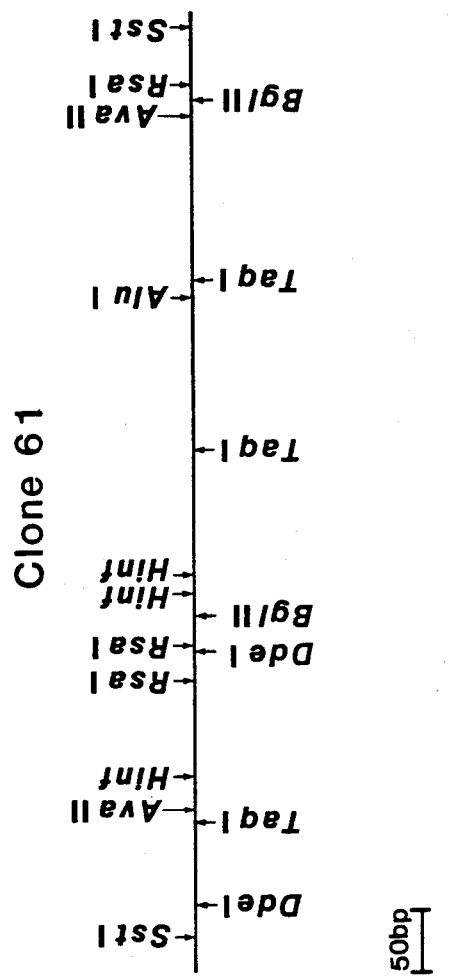
FIG. 3 represents a linear restriction map of clone 61.

FIG. 3 represents a linear restriction map of clone 61 obtained using various restriction enzymes as indicated.

FIG. 4 shows the nucleotide sequence of clone 61 obtained as described above with the corresponding amino acid sequence derived therefrom. The ATG 'start' codon and the TGA 'stop' codons are indicated by the boxes.

FIG. 5 shows the nucleotide sequences of the 572 bp AvaII and 432 bp BglII fragments thereof which also exhibit similar sequence homology as that of clone 61.

Clones 34 and 111 similarly exhibited partial or complete sequence homology between themselves and with some genomic clones which were not identical to those that hybridized to the clone 61 family, leading to the conclusion that clones 34 and 111 are part of another gene or family of genes which also encode human IL-2 or IL-2 like polypeptides.

The 420 bp Hae III-SstI fragment was prepared from clone 111 using standard procedures. This fragment was labeled with $-^{32}$p dCTP by nick translation using $E.$ $coli$ DNA polymerase I, according to the procedure of (R. Rigby et al., J. Mol. Biol. 113, 237-251.) The cDNA library was replicated onto nitrocellulose filters and the filters were processed and hybridized as described above except that the growth of the colonies was blocked with 100 µg/ml chloramphenicol to amplify the plasmid. (Hanahan, D., Meselson, M., Gene 10, 63-67. 1980). Filters containing the 1750 recombinant clones, were screened by hybridization to the 420 bp $^{32}$p-labeled HaeIII-SstI fragment from clone 111 in 50% formamide DNA hybridization buffer as described above. Two positive clones were identified in this experiment and designated as clones 111 and 34.

In all characterization experiments, clones 61 and 34 were treated as typical members of the two respective gene families.

EXAMPLE 6

Genomic Southern Blots Which Indicate An "IL-2 Family"

High molecular weight DNA was isolated from PBL's and tissue culture cells by the following procedure. All steps were done at 0°-4° C. unless otherwise specified.

Pelleted cells were washed once with PBS and 1×with IHB. The cells were then resuspended in IHB, NP-40 added to 0.5%, and the cells lysed by gentle vortexing. The nuclei were pelleted and resuspended in 100 mM Tris-HCl, 20 mM EDTA (pH 8.0) at a concentration of $10^7$ nuclei per ml. Self digested pronase was added to 500 µg/ml and SDS to 0.5%. The lysed nuclei were digested at 45° C. for 4 hours. The digest was then gently extracted 3×with TE-saturated phenol-chloroform and the DNA precipitated with 2 volumes of ethanol after the addition of NaCl to 0.2M. The DNA was washed 3×with 70% ethanol, 1×with 100% ethanol, dried briefly and dissolved in TE. Heat treated pancreatic ribonuclease was added to 50 µg/ml and the solution incubated for 2 hours at 37° C. Pronase and SDS were added as above and digestion continued for two hours. The DNA was then extracted and precipitated as above. After dissolving in TE, the DNA was dialyzed for 24 hours against 50 volumes of TE with two changes. After dialysis, aliquots of DNA were removed for restriction enzyme digests. Enzyme digests were carried out at 37° C. for 4 hours using twice the recommended amount of enzyme.

The digested DNA (10 µg) was electrophoresed on 1% agarose gels in standard buffer. After electrophoresis, the DNA fragments were partially depurinated in 0.25M HCl (Wahl et al., Proc. Natl. Acad. Sci., 76, 3683 (1979)) and then transferred to nitrocellulose paper by the method of Southern known to those skilled in the art.

The DNA blots were prehybridized for 4 hours at 42° C. against 50% formamide, 5×SSC, 20 mM sodium phosphate buffer, 2 ×Denhardt's, 200 µg/ml yeast RNA and 0.2% SDS (pH 7.0). The prehybridization buffer was removed and was replaced with the same buffer plus nick-translated AvaII fragment from clone 61 ($10^6$ cpm/ml, $1-2\times10^8$ cpm/ug). The hybridization was carried out for 16 hours at 42° C. The blots were then washed and autoradiographed.

Figure 6:
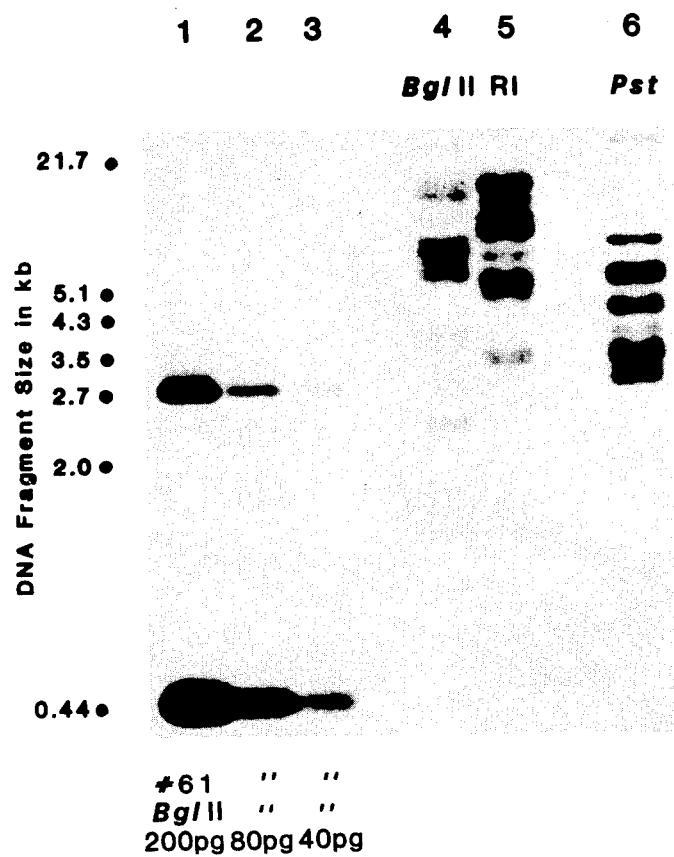
FIG. 6 shows a photograph of Southern blots of the genomic DNA using clone 61 as the probe.

FIG. 6 shows the results of the genomic Southern using PBL DNA. Lanes 1, 2 and 3 contain decreasing amounts of clone 61 digested with BglII and used as a standard. Lane 3 contains approximately one haploid genome equivalent of the genes encoded by clone 61. The most striking feature of this Southern blot is the large number of bands which appear in each genomic DNA digest. There are approximately 20 bands in the BglII digest and ~10 in both the EcoRI and Pst digest. Since BglII cuts once within the AvaII fragment of clone 61, 2 bands in a Southern blot would be expected if there were no introns (see FIG. 5). For the EcoRI and PstI digest, only one fragment would appear if there were no introns, since neither restriction enzyme has a site in clone 61. The large number of bands observed indicates that either the gene has a large number of introns or that there is a family of related genes which are very homologous at the DNA sequence level to clone 61 but have different restriction patterns.

The AvaII fragment of clone 61 was used as a probe to screen the human genomic library in bacteriophage lambda following the procedure described by Maniatis et al., (Molecular Cloning: A Laboratory Manual, Cold Spring Harbor 1982, pp. 320-321). By screening the genomic lambda bank with AvaII fragment, approximately 100 clones were found when only 3-4 would be expected for a single copy gene. The EcoRI patterns of several of the lambda clones were different from one another, corroborating the data from the genomic Southern blot where the EcoRI pattern was indicative of a family of genes.

Figure 12:
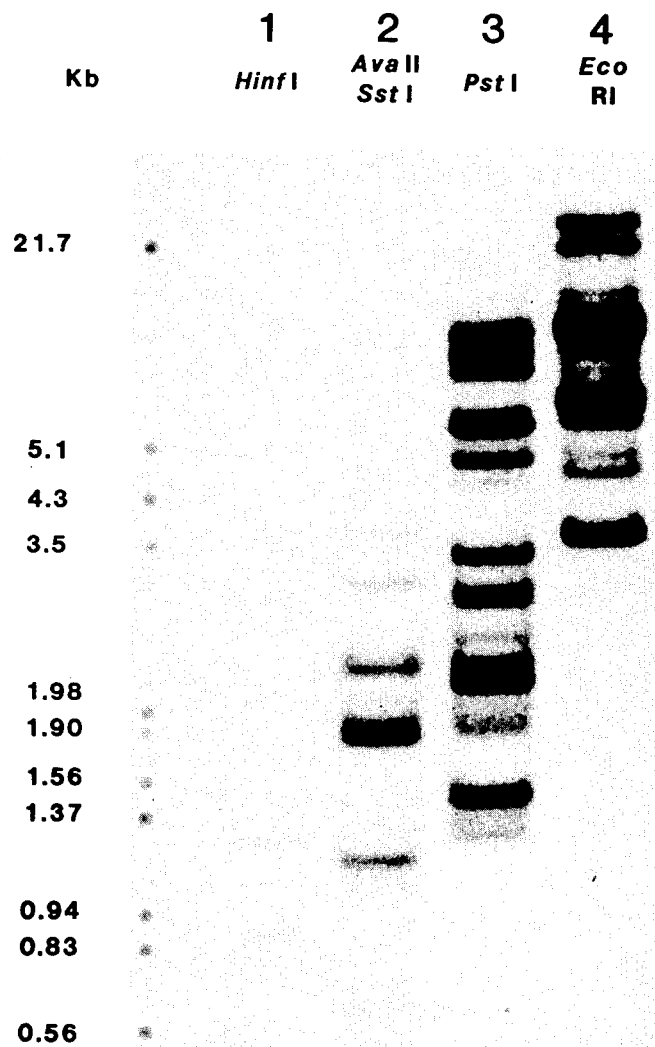
FIG. 12 is a photograph of the Southern blots of the genomic DNA using clone 34 as the probe.

FIG. 12 shows the results of the genomic Southern blots using PBL DNA hybridized to clone 34. Lanes 1, 2, 3 and 4 contain PBL DNA cleaved with different restriction enzymes. As with clone 61, the most striking feature of this Southern blot is the large number of bands which appear in each genomic digest. There are approximately 11 bands in the HinfI digest (lane 1), ~14 in the AvaII-SstI digest (lane 2), ~18 in the PstI digest (lane 3), and ~12 in the EcoRI digest (lane 4). Since EcoRI does not cut within clone 34, only one band would be expected to be seen in a Southern blot (see FIG. 13, the restriction map of clone 34); for the HinfI digest there would be four bands observed; three bands for the AvaII-SstI digest; and three bands for the PstI digest. The large number of bands actually observed indicates that either the gene has a large number of introns or that there is a family of related genes which are very homologous at the DNA sequence level, but have different restriction enzyme patterns. To distinguish between the two alternatives, several clones isolated (using clone 34 as a probe) from a human genomic library contained in bacteriophage lambda were characterized following the procedure described by Maniatis et al., (Molecular Cloning: A Laboratory Manual, Cold Spring Harbor 1982, pp. 320-321.) These characterized data indicate that clones 61 and 34 are members of families of "IL-2" like genes.

EXAMPLE 7

Expression of Clone 61 in E. coli

Figure 7:
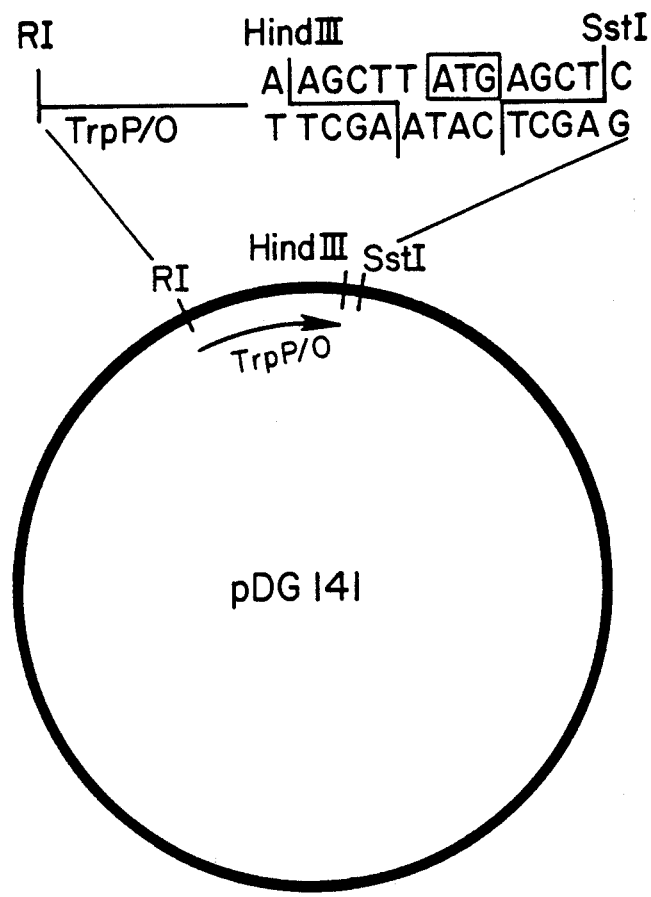
FIG. 7 shows plasmid DG141.
Figure 8:
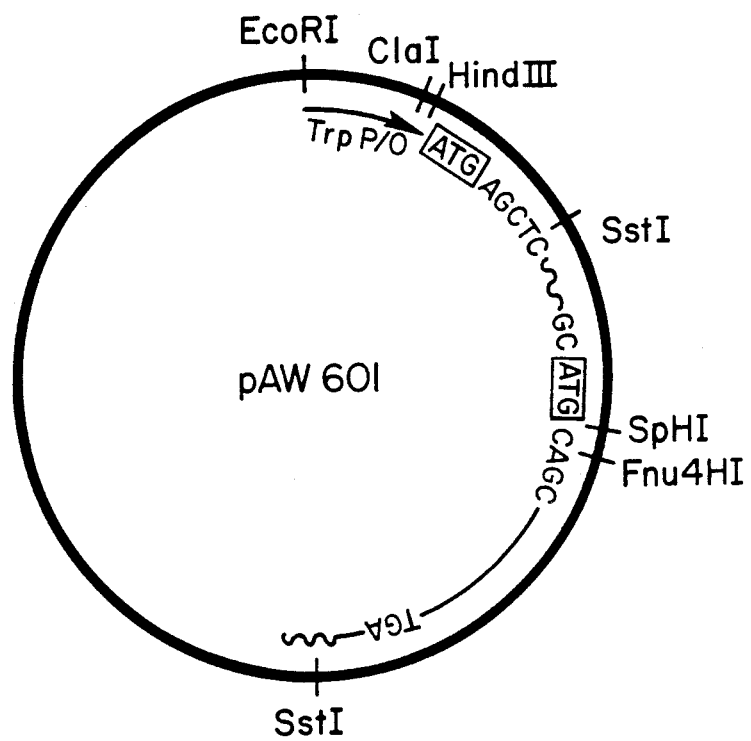
FIG. 8 shows the restriction pattern of clone pAW601, showing two SstI sites.

Clone 61 was digested with the restriction enzyme SstI and the DNA fragment containing the insert purified by electrophoresis on an agarose gel. The plasmid pDG141 (derivative of pBR322) containing the E. coli trp promoter (FIG. 7) was digested with the enzyme SstI and ligated with the purified insert from clone 61. The ligated DNA was transformed into competent E. coli cells and plated onto Ampicillin selection plates to select for transformants. Since the insert DNA can be ligated into the plasmid pDG141 in either orientation, the ligated transformants were analyzed by restriction enzyme mapping to screen for a clone where the ATG initiation codon was placed close to the trp promoter on pDG141. One such clone pAW601 was identified (FIG. 8).

Figure 9:
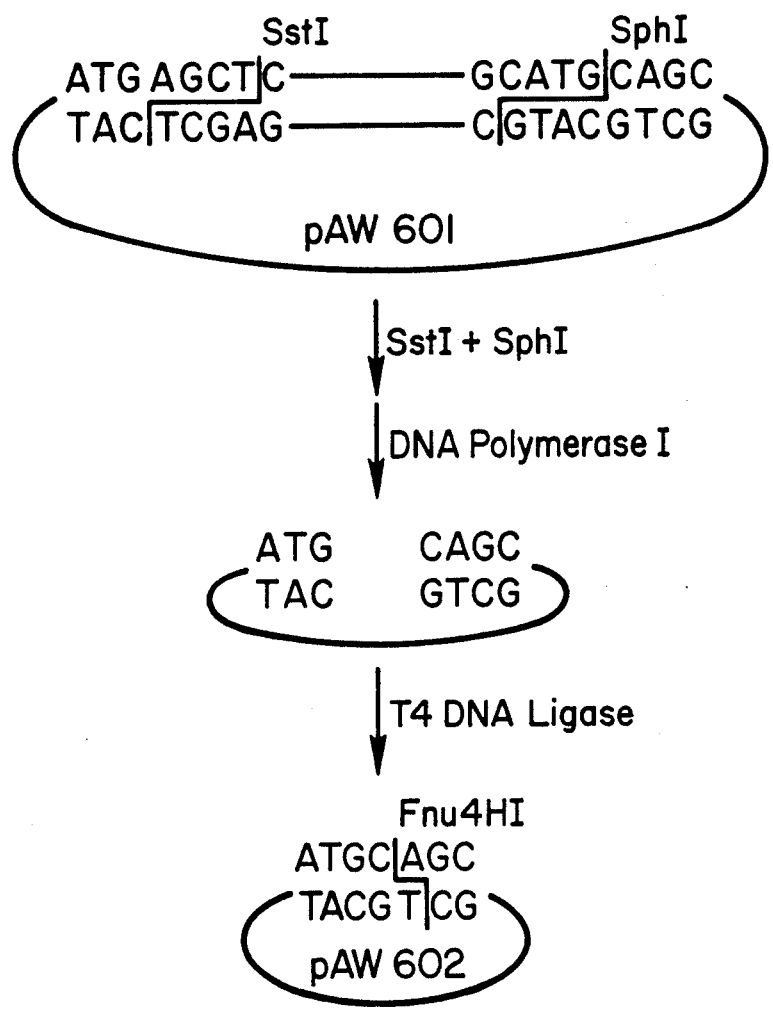
FIG. 9 represents a diagram of clone pAW602 showing a regeneration in pAW602 of the Fnu4HI site of pAW601.
Figure 10:
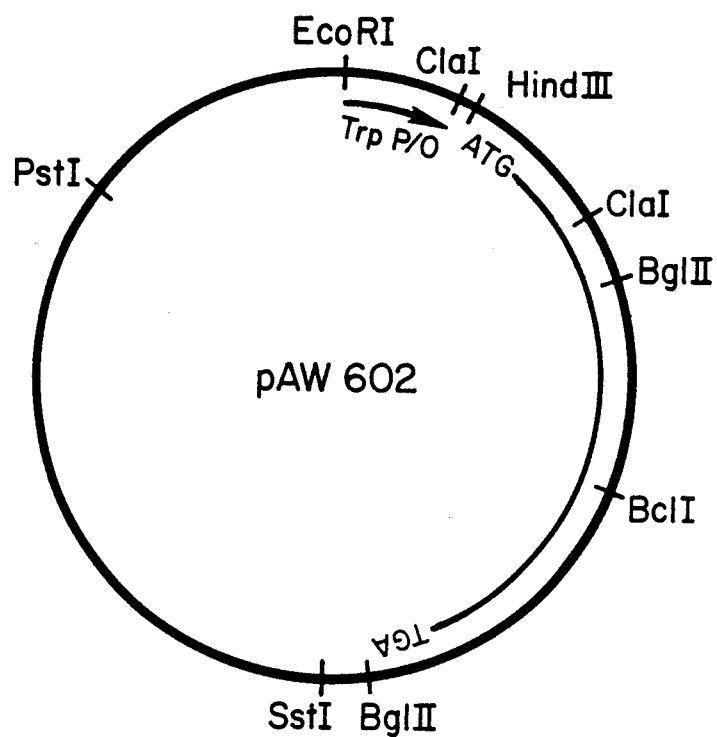
FIG. 10 represents a diagram of clone pAW602 showing various restriction sites.
Figure 11:
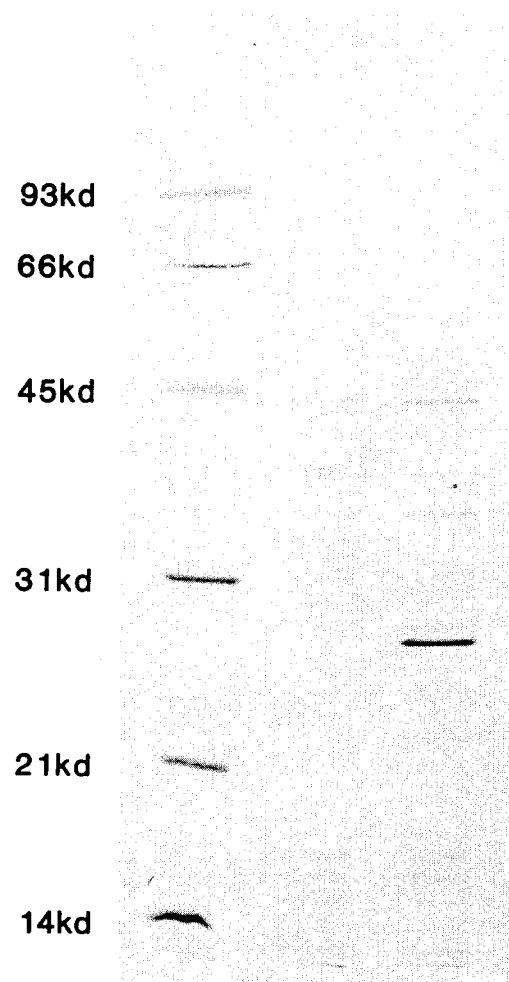
FIG. 11 is a photograph of the gel pattern showing the proteins produced by *E. coli* transformed with pAW602 or with Clone 61.

In order to express the protein efficiently, the ATG initiation codon has to be placed close to the ribosome binding site. In the case of pAW601 the distance between the ribosome binding site and the ATG-initiation codon is long. This distance can be shortened by making use of the SphI restriction site (GCATGC) and the SstI restriction site which is next to the ribosome binding site (FIG. 8). Since pAW601 has two SstI sites (FIG. 8), a partial digestion of the plasmid with SstI was necessary. This was accomplished by digesting the plasmid pAW601 with a small amount of the enzyme SstI for various lengths of time and the digested DNA analyzed on an agarose gel. The time point which permitted the maximum amount of circular DNA to be converted to linear molecules was chosen as the condition to be used for a preparative partial digestion of PAW601 with the enzyme SstI. The linear full length plasmid was purified from an agarose gel and further digested with the enzyme SphI, and the 3'-protruding ends of the SphI and SstI restriction sites were removed by treatment with the 3' to 5' exonuclease of E. coli DNA polymerase I to create blunt-ended DNA molecules. The plasmid DNA was then electrophoresed on an agarose gel and the largest DNA species recovered from the gel by electroelution. The eluted DNA was concentrated by ethanol precipitation and the two ends of the plasmid DNA ligated together by T4 DNA ligase. The ligated DNA was transformed into E. coli and the transformants screened for the regeneration of an Fnu4HI restriction site (FIG. 9). One such clone, pAW602 (FIG. 10) was selected for further analysis. Clone pAW602, and clone 61 were grown in minimal medium in the absence of tryptophan to derepress the trp promoter and cell-free extracts from these two clones analyzed on SDS-polyacrylamide gels (FIG. 11). One predominant protein band can be seen in the lane with extracts from pAW602 which is not present in the control lane with extracts from clone 61. The size of this protein was found to be about 26 k daltons and corresponds well with the size predicted from the amino acid sequence of clone 61.

EXAMPLE 8

Expression of Clone 34 in E. coli

Figure 13:
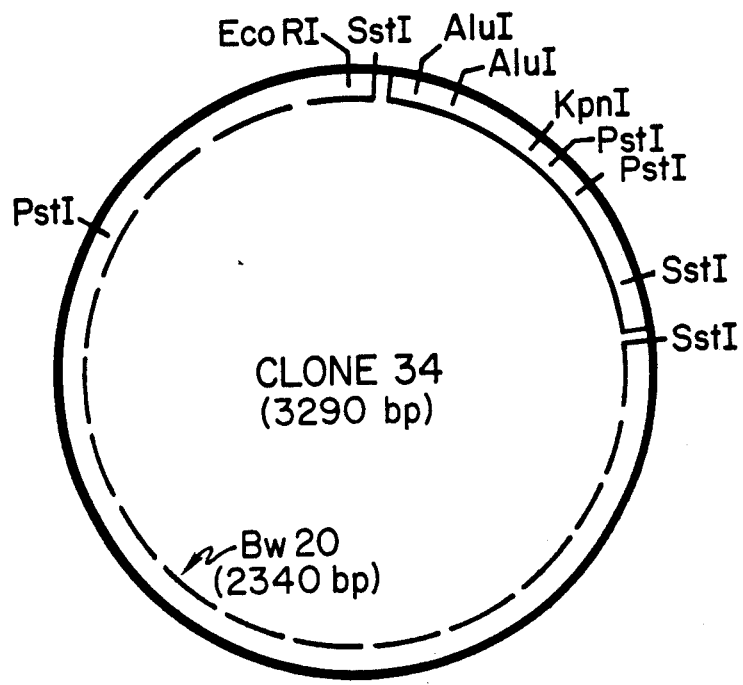
FIG. 13 shows a diagram of clone 34.
Figure 14:
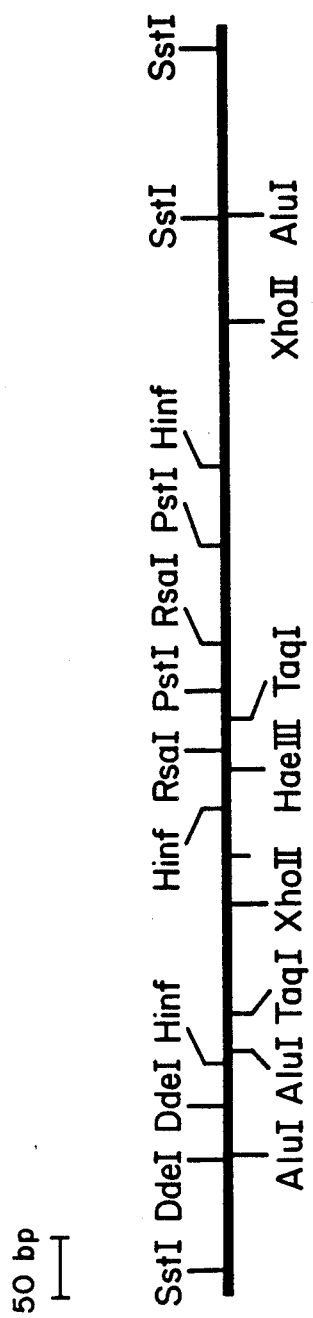
FIG. 14 shows the linear restriction map of clone 34.

Clone 34 was digested with the enzymes KpnI and EcoRI and the two DNA fragments purified on an agarose gel. FIG. 13 is a diagram showing the separation of the DNA fragments. The smaller DNA fragment containing the ATG-initiation codon (FIG. 14) was further digested with the enzyme AluI. There are three AluI sites in this DNA fragment and the 336 bp AluI-KpnI DNA fragment containing the initiation codon (FIGS. 14 and 15) is isolated by partial digestion of the EcorRI-KpnI fragment with a AluI enzyme for varying amounts of time to optimize the appearance of the 336 bp AluI-KpnI DNA fragment. This fragment was recovered by acrylamide gel fractionation.

The plasmid pDG141 (FIG. 7), containing the E. coli trp promoter, was digested with the enzyme SstI. The 3'-cohesive ends were removed and made into blunt ended DNA molecules by treatment with 3' exonuclease of DNA Polymerase I Klenow fragment. This plasmid DNA was then digested with EcoRI and the small DNA fragment containing the E. coli trp promoter was purified and recovered by acrylamide gel fractionation.

Figure 16:
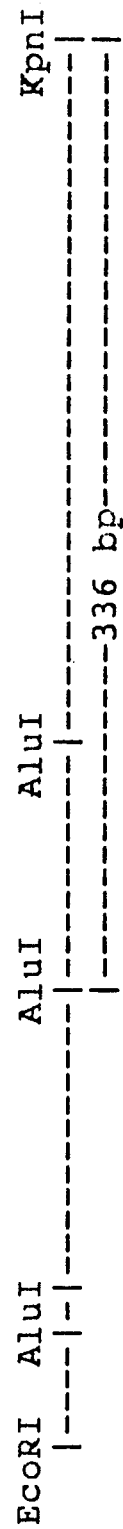
FIG. 16 is a diagram of the 336 bp AluI-KpnI fragment of clone 34.

Equimolar amounts of the E. coli trp promoter fragment, the 336 bp AluI-KpnI fragment and the large KpnI-EcoRI fragment containing the carboxy-terminal coding region of clone 34 were ligated together by using T4 DNA ligase. Competent E. coli cells were then transformed with the ligated plasmid. The resulting transformants were checked by restriction enzyme mapping for the correct ligation of the various DNA fragments. One such clone was identified (pSY2601) as shown in FIG. 16. Clone pSY2601 has two ATG-initiation codons that are in phase with the protein sequence deduced for clone 34 (FIG. 16). The first ATG originated from the trp promoter fragment of pDG141 (FIG. 7), and the second ATG is the initiation codon of clone 34 (FIG. 13). Since both of these ATGs are in the same translational reading frame, the first initiation codon will be utilized by the cell because of its close proximity to the ribosome binding site, to synthesize a fused protein eight amino acids longer than the protein encoded by clone 34. The initiation codon for clone 34 can be placed closer to the trp promoterribosome binding site by taking advantagte of the presence of a unique HindIII restriction site and the action of T4 DNA polymerase.

Figure 17:
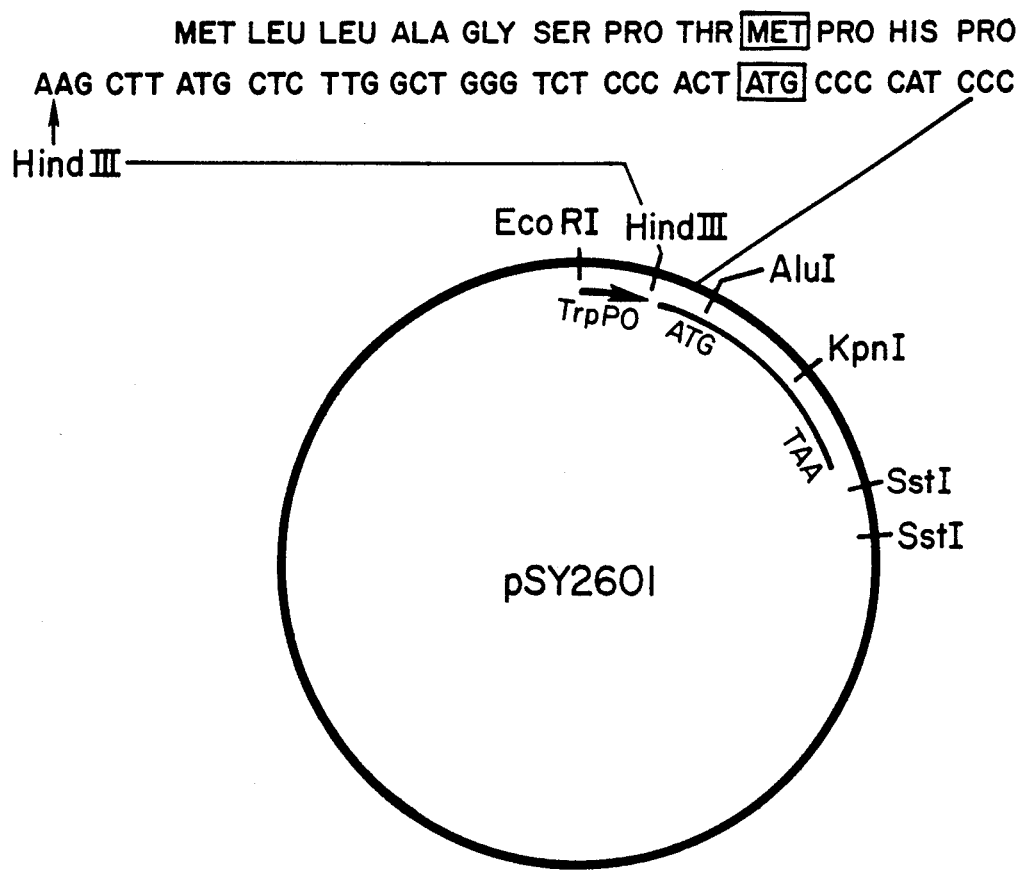
FIG. 17 represents a diagram of clone pSY2601.

Clone pSY2601 was digested with the enzyme HindIII to linearize the plasmid. It was then subjected to the action of T4 DNA polymerase in the presence of dCTP, as described by Maniatis et al. ("Molecular Cloning", Cold Spring Harbor, N.Y., p.117-121. (1981)). The 3'-exonuclease of T4 DNA polymerase degrades the 3' strand of clone pSY2601 until it exposes a base complementary to the added dCTP, then a series of synthesis and degradation steps occurs at that position. The DNA is not degraded any further (FIG. 17). The DNA was then extracted with phenol, passed through a gel filtration column to remove unincorporated dCTP, and subjected to a second round of T4 DNA Polymerase reaction in the presence of dTTP. After S1 nuclease treatment of the DNA to remove the single-stranded 5'-protruding end, the resulting molecule has a blunt end with three additional base pairs before the ATG-initiation codon of clone 34 (FIG. 17). The DNA was thereafter digested with EcoRI to remove the partially degraded trp promoter fragment, and the large plasmid containing the clone 34 gene purified on an agarose gel.

The ptrp3 DNA (FIG. 18) was digested with the enzyme HindIII, the cohesive end removed by S1 nuclease treatment, and then digested with the enzyme EcoRI to liberate a small fragment, with an EcoRI cohesive end and a blunt end containing the trp promoter. This promoter fragment was ligated to the T4

Figure 19:
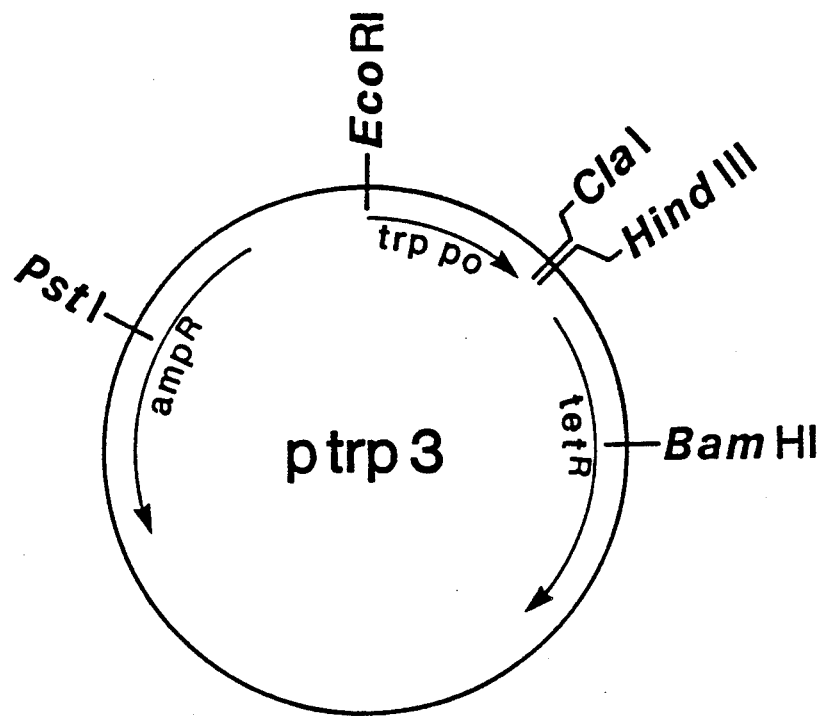
FIG. 19 shows the restriction pattern of ptrp3 DNA.
Figure 20:
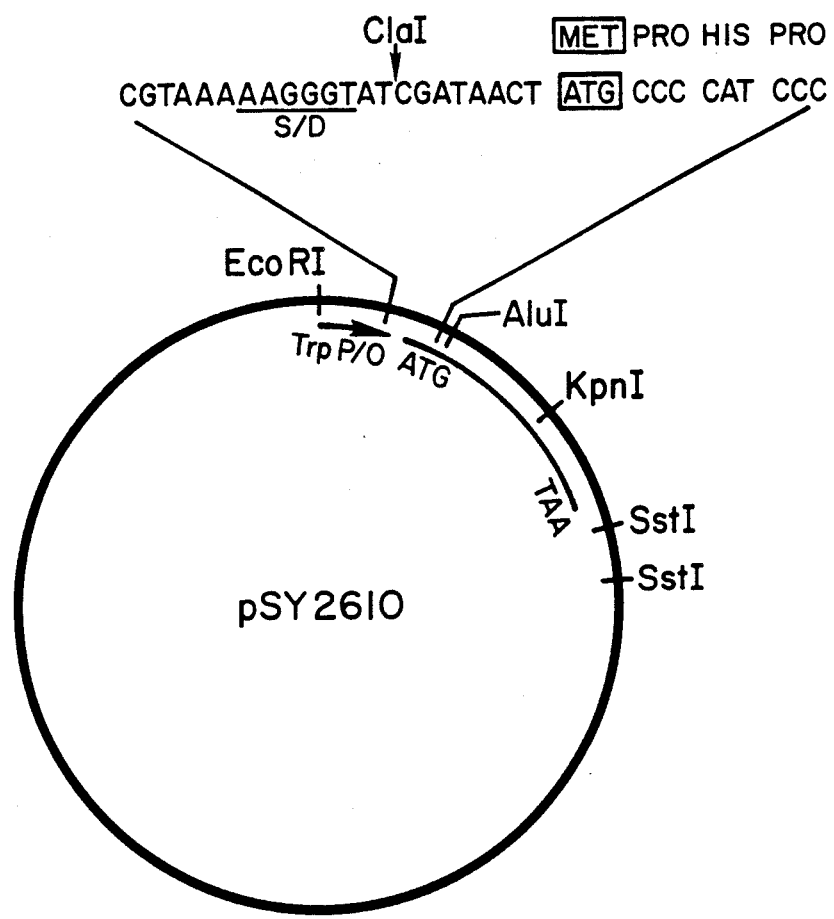
FIG. 20 is a diagram of plasmid pSY2610.

DNA polymerase treated plasmid containing the clone 34 gene by action of T4 ligase. The ligated DNA was then transformed into competent *E. coli* cells and the transformants screened by restriction mapping. One clone was identified as pSY2610 and the nucleic acid sequence near the 5' end of the gene confirmed as shown in FIG. 19.

EXAMPLE 9

Oocyte Assay of Biological Activity of IL-2

The assay for IL-2 activity was performed essentially as described in Example 2.

Although the DNA fragments and inserts described above were obtained or derived from natural sources, the DNA fragments and inserts may also be synthesized chemically in whole or in part or semisynthetically constituted by methods known in the art.

The instant invention thus provides DNA sequences which may be from any source, including natural, synthetic and semisynthetic sequences, which hybridize with an exhibit partial or complete homology with DNA sequences derived from IL-2 mRNA obtained by induction of human PBLs with appropriate mitogens.

IL-2 is useful in the diagnosis and treatment of bacterial, viral, parasitic, protozoan and fungal infections; in manifestations of lymphokine or immunodeficiency; for reconstitution of normal immunofunction in aged humans and animals; in the development of diagnostic assays such as those employing enzyme amplification, radiolabelling, radioimaging, and other methods known in the art for monitoring IL-2 levels in the diseased state; for the promotion of T-cell growth in vitro for therapeutic and diagnostic purposes; for blocking receptor sites for lymphokines; and in various other therapeutic, diagnostic and research applications. The various therapeutic and diagnostic applications of human IL-2 have been investigated and reported in S. A. Rosenberg; E. A. Grimm et al., A. Mazumder et al., and E. A. Grimm and S. A. Rosenberg, which publications are incorporated herein by reference and made a part hereof. The polypeptides of the subject invention may be used by themselves or in combination with other immunologically relevant B or T-cells or other therapeutic agents. For therapeutic or diagnostic applications, they may be formulated in nontoxic, nonallergenic, physiologically compatible carrier media such as distilled water, Ringer's solution, Hand's solution, physiological saline and the like. Administrations of the subject polypeptide formulations to humans or animals may be oral or intraperitoneal or intramuscular or subcutaneous as deemed appropriate by the physician. Examples of relevant cells are B or T-cells, natural killer cells, and the like and exemplary therapeutic reagents which may be used in combination with the polypeptides of this invention are the various interferons, especially gamma interferon, B cell growth factor, IL-1 and the like. A. Mazumder et al., in press.

The foregoing description of a preferred embodiment of the invention has been presented for purposes of illustration and description. It is not intended to be exhaustive or to limit the invention to the precise form disclosed, and obviously many modifications and variations are possible in light of the above teaching. The particular embodiment was chosen and described in order to best explain the principles of the invention and its practical application, to thereby enable others skilled in the art to best utilize the invention in various embodiments as are suited to the particular use contemplated. It is intended that the scope of the invention be defined by the claims appended hereto.

What is claimed is:

1. A messenger RNA preparation capable of producing IL-2 in a *Xenopus laevis* oocyte translation system prepared by a process which comprises
recovering an mRNA preparation which preparation has been hybridized to a recombinant DNA useful for enriching mRNA encoding IL-2 comprising the sequence

```
         10         20         30
TCCTGAGGAA CAGACTTAAG TATGCCCTGA
         40         50         60
CAGGAGATGA AGTAAAGAAG ATTTGCATGC
         70         80         90
AGCGGTTCAT TAAAATCGAT GGCAAGGTCC
        100        110        120
GAACTGATAT AACCTACCCT GCTGGATTCA
        130        140        150
TGGATGTCAT CAGCATTGAC AAGACGGGAG
        160        170        180
AGAATTTCCG TCTGATCTAT GACACCAAGG
        190        200        210
GTCGCTTTGC TGTACATCGT ATTACACCTG
        220        230        240
AGGAGGCCAA GTACAAGTTG TGCAAAGTGA
        250        260        270
GAAAGATCTT TGTGGGCACA AAAGGAATCC
        280        290        300
CTCATCTGGT GACTCATGAT GCCCGCACCA
        310        320        330
TCCGCTACCC CGATCCCCTC ATCAAGGTGA
        340        350        360
ATGATACCAT TCAGATTGAT TTAGAGACTG
        370        380        390
GCAAGATTAC TGATTTCATC AAGTTCGACA
        400        410        420
CTGGTAACCT GTGTATGGTG ACTGGAGGTG
        430        440        450
CTAACCTAGG AAGAATTGGT GTGATCACCA
        460        470        480
ACAGAGAGAG GCACCCTGGA TCTTTTGACG
        490        500        510
TGGTTCACGT GAAAGATGCC AATGGCAACA
        520        530        540
GCTTTGCCAC TCGACTTTCC AACATTTTTG
        550        560        570
TTATTGGCAA GGGCAACAAA CCATGGATTT
        580        590        600
CTCTTCCCCG AGGAAAGGGT ATCCGCCTCA
        610        620        630
CCATTGCTGA AGAGAGAGAC AAAAGACTGG
        640        650        660
CGGCCAAACA GAGCAGTGGG TGAAATGGGT
        670        680        690
CCCTGGTGAC ATGTCAGATC TTTGTACGTA
        700        710        720
ATTAAAAATA TTGTGGCAGG ATTAATAGC.
``` or

```
         90        100        110        120
GTCC GAACTGATAT AACCTACCCT GCTGGATTCA
        130        140        150
TGGATGTCAT CAGCATTGAC AAGACGGGAG
        160        170        180
AGAATTTCCG TCTGATCTAT GACACCAAGG
        190        200        210
GTCGCTTTGC TGTACATCGT ATTACACCTG
        220        230        240
AGGAGGCCAA GTACAAGTTG TGCAAAGTGA
        250        260        270
GAAAGATCTT TGTGGGCACA AAAGGAATCC
        280        290        300
CTCATCTGGT GACTCATGAT GCCCGCACCA
        310        320        330
TCCGCTACCC CGATCCCCTC ATCAAGGTGA
        340        350        360
ATGATACCAT TCAGATTGAT TTAGAGACTG
```

-continued

```
            370          380          390
GCAAGATTAC TGATTTCATC AAGTTCGACA
            400          410          420
CTGGTAACCT GTGTATGGTG ACTGGAGGTG
            430          440          450
CTAACCTAGG AAGAATTGGT GTGATCACCA
            460          470          480
ACAGAGAGAG GCACCCTGGA TCTTTTGACG
            490          500          510
TGGTTCACGT GAAAGATGCC AATGGCAACA
            520          530          540
GCTTTGCCAC TCGACTTTCC AACATTTTTG
            550          560          570
TTATTGGCAA GGGCAACAAA CCATGGATTT
            580          590          600
CTCTTCCCCG AGGAAAGGGT ATCCGCCTCA
            610          620          630
CCATTGCTGA AGAGAGAGAC AAAAGACTGG
            640          650          660
CGGCCAAACA GAGCAGTGGG TGAAATGG
``` or

```
            250          260          270
GATCTT TGTGGGCACA AAAGGAATCC
            280          290          300
CTCATCTGGT GACTCATGAT GCCCGCACCA
            310          320          330
TCCGCTACCC CGATCCCCTC ATCAAGGTGA
            340          350          360
ATGATACCAT TCAGATTGAT TTAGAGACTG
            370          380          390
GCAAGATTAC TGATTTCATC AAGTTCGACA
            ·400          410          420
CTGGTAACCT GTGTATGGTG ACTGGAGGTG
            430          440          450
CTAACCTAGG AAGAATTGGT GTGATCACCA
            460          470          480
ACAGAGAGAG GCACCCTGGA TCTTTTGACG
            490          500          510
TGGTTCACGT GAAAGATGCC AATGGCAACA
            520          530          540
GCTTTGCCAC TCGACTTTCC AACATTTTTG
            550          560          570
TTATTGGCAA GGGCAACAAA CCATGGATTT
            580          590          600
CTCTTCCCCG AGGAAAGGGT ATCCGCCTCA
            610          620          630
CCATTGCTGA AGAGAGAGAC AAAAGACTGG
            640          650          660
CGGCCAAACA GAGCAGTGGG TGAAATGGGT
            670
CCCTGGTGAC ATGTCA;
``` or their complements,
under conditions wherein the hybridization buffer contains 50% formamide and 800 mM NaCl and wherein hybridization has been conducted at 37° C. for 14–16 hours.

2. A messenger RNA preparation capable of producing IL-2 in a *Xenopus laevis* oocyte translation system prepared by a process which comprises
recovering an mRNA preparation which preparation has been hybridized to a recombinant DNA useful for enriching mRNA encoding IL-2 comprising the sequence

```
            10           20           30
AAAAAACAAA ACCAAAACAT TCCGAAAATG
            40           50           70
TCCACAGCCT CACGCCTACC TGCCCTTACC
            70           80           90
CTCAGCTCTT GGCTGGGTCT CCCACTATGC
            100          110          120
CCCATCCCTC CTTCCCTCAG AGGCTGGGTG
            130          140          150
CCAGAGGGTG GATGAGAAGA GATTCTCAAA
            160          170          180
GCTGGGCAGG TCCCAGGAAA AGCCACTTGA
            190          200          210
TCGACCTGGG CAGTGAGGGG AAGCAGGGGGG
            220          230          240
TGGGGGGTGG GGTGGGGAGG TGGTGGGGGG
            250          260          270
AGCCAGATGA GATGTTCTCC GACATCTACA
            280          290          300
AGATCCGGGA GATCGCGGAC GGGTTGTGCC
            310          320          330
TGGAGGTGGA GGGGAAGATG GTCAGTAGGA
            340          350          360
CAGAAGGTAA CATTGATGAC TCGCTCATTG
            370          380          390
GTGGAAATGC CTCCGCTGAA GGCCCCGAGG
            400          410          420
GCGAAGGTAC CGAAAGCACA GTAATCACTG
            430          440          450
GTGTCGATAT TGTCATGAAC CATCACCTGC
            460          470          480
AGGAAACAAG TTTCACAAAA GAAGCCTACA
            490          500          510
AGAAGTACAT CAAAGATTAC ATGAAATCAA
            520          530          540
TCAAAGGGAA ACTTGAAGAA CAGAGACCAG
            550          560          570
AAAGAGTAAA ACCTTTTATG ACAGGGGCTG
            580          590          600
CAGAACAAAT CAAGCACATC CTTGCTAATT
            610          620          630
TCAAAAACTA CCAGTTCTTT ATTGGTGAAA
            640          650          660
ACATGAATCC AGATGGCATG GTTGCTCTAT
            670          680          690
TGGACTACCG TGAGGATGGT GTGACCCCAT
            700          710          720
ATATGATTTT CTTTAAGGAT GGTTTAGAAA
            730          740          750
TGGAAAAATG TTAACAAATG TGGCAATTAT
            760          770          780
TTTGGATCTA TCACCTGTCA TCATAACTGG
            790          800          810
CTTCTGCTTG TCATCCACAC AACACCAGGA
            820          830          840
CTTAAGACAA ATGGGACTGA TGTCATCTTG
            850          860          870
AGCTCTTCAT TTATTTTGAC TGTGATTTAT
            880          890          900
TTGGAGTGGA GGCATTGTTT TTAAGAAAAA
            910          920          930
CATGTCATGT AGGTTGTCTA AAAATAAAAT
            940
GCATTTAAAC TC
``` or

```
310          320          330'         340
A GGGGAAGATG GTCAGTAGGA CAGAAGGTAA
            350          360          370
CATTGATGAC TCGCTCATTG GTGGAAATGC
            380          390          400
CTCCGCTGAA GGCCCCGAGG GCGAAGGTAC
            410          420          430
CGAAAGCACA GTAATCACTG GTGTCGATAT
            440          450          460
TGTCATGAAC CATCACCTGC AGGAAACAAG
            470          480          490
TTTCACAAAA GAAGCCTACA AGAAGTACAT
            500          510          520
CAAAGATTAC ATGAAATCAA TCAAAGGGAA
            530          540          550
ACTTGAAGAA CAGAGACCAG AAAGAGTAAA
            560          570          580
ACCTTTTATG ACAGGGGCTG CAGAACAAAT
            590          600          610
CAAGCACATC CTTGCTAATT TCAAAAACTA
            620          630          640
CCAGTTCTTT ATTGGTGAAA ACATGAATCC
            650          660          670
AGATGGCATG GTTGCTCTAT TGGACTACCG
            680          690          700
TGAGGATGGT GTGACCCCAT ATATGATTTT
            710          720          730
CTTTAAGGAT GGTTTAGAAA TGGAAAAATG
```

-continued

```
            740           750           760
TTAACAAATG TGGCAATTAT TTTGGATCTA
            770           780           790
TCACCTGTCA TCATAACTGG CTTCTGCTTG
            800           810           820
TCATCCACAC AACACCAGGA CTTAAGACAA
            830           840           850
ATGGGACTGA TGTCATCTTG AGCTCTTCAT
            860           870           880
TTATTTTGAC TGTGATTTAT TTGGAGTGGA
            890           900           910
GGCATTGTTT TTAAGAAAAA CATGTCATGT
            920           930           940
AGGTTGTCTA AAAATAAAAT GCATTTAAAC TC
``` or their complements, under conditions wherein the hybridization buffer contains 50% formamide and 800 mM NaCl and wherein hybridization has been conducted at 37° C. for 14–16 hours.

3. An mRNA preparation free of human cells and enriched in mRNA encoding a protein which exhibits IL-2 activity, which mRNA preparation hybridizes to a recombinant DNA useful for enriching mRNA encoding IL-2 comprising the sequence

```
             10            20            30
TGGTGAGGAA CAGACTTAAG TATGCCCTGA
             40            50            60
CAGGAGATGA AGTAAAGAAG ATTTGCATGC
             70            80            90
AGCGGTTCAT TAAAATCGAT GGCAAGGTCC
            100           110           120
GAACTGATAT AACCTACCCT GCTGGATTCA
            130           140           150
TGGATGTCAT CAGCATTGAC AAGACGGGAG
            160           170           180
AGAATTTCCG TCTGATCTAT GACACCAAGG
            190           200           210
GTCGCTTTGC TGTACATCGT ATTACACCTG
            220           230           240
AGGAGGCCAA GTACAAGTTG TGCAAAGTGA
            250           260           270
GAAAGATCTT TGTGGGCACA AAAGGAATCC
            280           290           300
CTCATCTGGT GACTCATGAT GCCCGCACCA
            310           320           330
TCCGCTACCC CGATCCCCTC ATCAAGGTGA
            340           350           360
ATGATACCAT TCAGATTGAT TTAGAGACTG
            370           380           390
GCAAGATTAC TGATTTCATC AAGTTCGACA
            400           410           420
CTGGTAACCT GTGTATGGTG ACTGGAGGTG
            430           440           450
CTAACCTAGG AAGAATTGGT GTGATCACCA
            460           470           480
ACAGAGAGAG GCACCCTGGA TCTTTTGACG
            490           500           510
TGGTTCACGT GAAAGATGCC AATGGCAACA
            520           530           540
GCTTTGCCAC TCGACTTTCC AACATTTTTG
            550           560           570
TTATTGGCAA GGGCAACAAA CCATGGATTT
            580           590           600
CTCTTCCCCG AGGAAAGGGT ATCCGCCTCA
            610           620           630
CCATTGCTGA AGAGAGAGAC AAAAGACTGG
            640           650           660
CGGCCAAACA GAGCAGTGGG TGAAATGGGT
            670           680           690
CCCTGGTGAC ATGTCAGATC TTTGTACGTA
            700           710           720
ATTAAAAATA TTGTGGCAGG ATTAATAGC,
``` or

```
             90           100           110           120
GTCC GAACTGATAT AACCTACCCT GCTGGATTCA
            130           140           150
TGGATGTCAT CAGCATTGAC AAGACGGGAG
            160           170           180
AGAATTTCCG TCTGATCTAT GACACCAAGG
            190           200           210
GTCGCTTTGC TGTACATCGT ATTACACCTG
            220           230           240
AGGAGGCCAA GTACAAGTTG TGCAAAGTGA
            250           260           270
GAAAGATCTT TGTGGGCACA AAAGGAATCC
            280           290           300
CTCATCTGGT GACTCATGAT GCCCGCACCA
            310           320           330
TCCGCTACCC CGATCCCCTC ATCAAGGTGA
            340           350           360
ATGATACCAT TCAGATTGAT TTAGAGACTG
            370           380           390
GCAAGATTAC TGATTTCATC AAGTTCGACA
            400           410           420
CTGGTAACCT GTGTATGGTG ACTGGAGGTG
            430           440           450
CTAACCTAGG AAGAATTGGT GTGATCACCA
            460           470           480
ACAGAGAGAG GCACCCTGGA TCTTTTGACG
            490           500           510
TGGTTCACGT GAAAGATGCC AATGGCAACA
            520           530           540
GCTTTGCCAC TCGACTTTCC AACATTTTTG
            550           560           570
TTATTGGCAA GGGCAACAAA CCATGGATTT
            580           590           600
CTCTTCCCCG AGGAAAGGGT ATCCGCCTCA
            610           620           630
CCATTGCTGA AGAGAGAGAC AAAAGACTGG
            640           650           660
CGGCCAAACA GAGCAGTGGG TGAAATGG
``` or

```
            250           260           270
GATCTT TGTGGGCACA AAAGGAATCC
            280           290           300
CTCATCTGGT GACTCATGAT GCCCGCACCA
            310           320           330
TCCGCTACCC CGATCCCCTC ATCAAGGTGA
            340           350           360
ATGATACCAT TCAGATTGAT TTAGAGACTG
            370           380           390
GCAAGATTAC TGATTTCATC AAGTTCGACA
            400           410           420
CTGGTAACCT GTGTATGGTG ACTGGAGGTG
            430           440           450
CTAACCTAGG AAGAATTGGT GTGATCACCA
            460           470           480
ACAGAGAGAG GCACCCTGGA TCTTTTGACG
            490           500           510
TGGTTCACGT GAAAGATGCC AATGGCAACA
            520           530           540
GCTTTGCCAC TCGACTTTCC AACATTTTTG
            550           560           570
TTATTGGCAA GGGCAACAAA CCATGGATTT
            580           590           600
CTCTTCCCCG AGGAAAGGGT ATCCGCCTCA
            610           620           630
CCATTGCTGA AGAGAGAGAC AAAAGACTGG
            640           650           660
CGGCCAAACA GAGCAGTGGG TGAAATGGGT
            670
CCCTGGTGAC ATGTCA.
``` or their complements, under conditions wherein the hybridization buffer contains 50% formamide and 800 mM NaCl, and the hybridization is conducted at 37° C. for 14–16 hours.

4. A host cell injected with the mRNA of claim 3.

5. The host cell of claim 4 which is a *Xenopus laevis* oocyte.

6. An mRNA preparation free of human cells and enriched in mRNA encoding a protein which exhibits IL-2 activity, which mRNA preparation hybridizes to a recombinant DNA useful for enriching mRNA encoding IL-2 comprising the sequence

```
          10          20          30
AAAAAACAAA ACCAAAACAT TCCGAAAATG
          40          50          60
TCCACAGCCT CACGCCTACC TGCCCTTACC
          70          80          90
CTCAGCTCTT GGCTGGGTCT CCCACTATGC
         100         110         120
CCCATCCCTC CTTCCCTCAG AGGCTGGGTG
         130         140         150
CCAGAGGGTG GATGAGAAGA GATTCTCAAA
         160         170         180
GCTGGGCAGG TCCCAGGAAA AGCCACTTGA
         190         200         210
TCGACCTGGG CAGTGAGGGG AAGCAGGGGG
         220         230         240
TGGGGGGTGG GGTGGGGAGG TGGTGGGGGG
         250         260         270
AGCCAGATGA GATGTTCTCC GACATCTACA
         280         290         300
AGATCCGGGA GATCGCGGAC GGGTTGTGCC
         310         320         330
TGGAGGTGGA GGGGAAGATG GTCAGTAGGA
         340         350         360
CAGAAGGTAA CATTGATGAC TCGCTCATTG
         370         380         390
GTGGAAATGC CTCCGCTGAA GGCCCCGAGG
         400         410         420
GCGAAGGTAC CGAAAGCACA GTAATCACTG
         430         440         450
GTGTCGATAT TGTCATGAAC CATCACCTGC
         460         470         480
AGGAAACAAG TTTCACAAAA GAAGCCTACA
         490         500         510
AGAAGTACAT CAAAGATTAC ATGAAATCAA
         520         530         540
TCAAAGGGAA ACTTGAAGAA CAGAGACCAG
         550         560         570
AAAGAGTAAA ACCTTTTATG ACAGGGGCTG
         580         590         600
CAGAACAAAT CAAGCACATC CTTGCTAATT
         610         620         630
TCAAAAACTA CCAGTTCTTT ATTGGTGAAA
         640         650         660
ACATGAATCC AGATGGCATG GTTGCTCTAT
         670         680         690
TGGACTACCG TGAGGATGGT GTGACCCCAT
         700         710         720
ATATGATTTT CTTTAAGGAT GGTTTAGAAA
         730         740         750
TGGAAAAATG TTAACAAATG TGGCAATTAT
         760         770         780
TTTGGATCTA TCACCTGTCA TCATAACTGG
         790         800         810
CTTCTGCTTG TCATCCACAC AACACCAGGA
         820         830         840
CTTAAGACAA ATGGGACTGA TGTCATCTTG
         850         860         870
AGCTCTTCAT TTATTTTGAC TGTGATTTAT
         880         890         900
TTGGAGTGGA GGCATTGTTT TTAAGAAAAA
         910         920         930
CATGTCATGT AGGTTGTCTA AAAATAAAAT
         940
GCATTTAAAC TC
``` or

```
         310         320         330         340
 A GGGGAAGATG GTCAGTAGGA CAGAAGGTAA
         350         360         370
CATTGATGAC TCGCTCATTG GTGGAAATGC
         380         390         400
CTCCGCTGAA GGCCCCGAGG GCGAAGGTAC
         410         420         430
CGAAAGCACA GTAATCACTG GTGTCGATAT
         440         450         460
TGTCATGAAC CATCACCTGC AGGAAACAAG
         470         480         490
TTTCACAAAA GAAGCCTACA AGAAGTACAT
         500         510         520
CAAAGATTAC ATGAAATCAA TCAAAGGGAA
         530         540         550
ACTTGAAGAA CAGAGACCAG AAAGAGTAAA
         560         570         580
ACCTTTTATG ACAGGGGCTG CAGAACAAAT
         590         600         610
CAAGCACATC CTTGCTAATT TCAAAAACTA
         620         630         640
CCAGTTCTTT ATTGGTGAAA ACATGAATCC
         650         660         670
AGATGGCATG GTTGCTCTAT TGGACTACCG
         680         690         700
TGAGGATGGT GTGACCCCAT ATATGATTTT
         710         720         730
CTTTAAGGAT GGTTTAGAAA TGGAAAAATG
         740         750         760
TTAACAAATG TGGCAATTAT TTTGGATCTA
         770         780         790
TCACCTGTCA TCATAACTGG CTTCTGCTTG
         800         810         820
TCATCCACAC AACACCAGGA CTTAAGACAA
         830         840         850
ATGGGACTGA TGTCATCTTG AGCTCTTCAT
         860         870         880
TTATTTTGAC TGTGATTTAT TTGGAGTGGA
         890         900         910
GGCATTGTTT TTAAGAAAAA CATGTCATGT
         920         930         940
AGGTTGTCTA AAAATAAAAT GCATTTAAAC TC
``` or their complements, under conditions wherein the hybridization buffer contains 50% formamide and 800 mM NaCl, and the hybridization is conducted at 37° C. for 14–16 hours.

7. A host cell injected with the mRNA of claim 6.

8. The host cell of claim 7 which is a *Xenopus laevis* oocyte.

9. A recombinant DNA useful for enriching mRNA encoding IL-2 comprising a recombinant DNA of the sequence

```
          10          20          30
TCCTGAGGAA CAGACTTAAG TATGCCCTGA
          40          50          60
CAGGAGATGA AGTAAAGAAG ATTTGCATGC
          70          80          90
AGCGGTTCAT TAAAATCGAT GGCAAGGTCC
         100         110         120
GAACTGATAT AACCTACCCT GCTGGATTCA
         130         140         150
TGGATGTCAT CAGCATTGAC AAGACGGGAG
         160         170         180
AGAATTTCCG TCTGATCTAT GACACCAAGG
         190         200         210
GTCGCTTTGC TGTACATCGT ATTACACCTG
         220         230         240
AGGAGGCCAA GTACAAGTTG TGCAAAGTGA
         250         260         270
GAAAGATCTT TGTGGGCACA AAAGGAATCC
         280         290         300
CTCATCTGGT GACTCATGAT GCCCGCACCA
         310         320         330
TCCGCTACCC CGATCCCCTC ATCAAGGTGA
         340         350         360
ATGATACCAT TCAGATTGAT TTAGAGACTG
         370         380         390
GCAAGATTAC TGATTTCATC AAGTTCGACA
         400         410         420
CTGGTAACCT GTGTATGGTG ACTGGAGGTG
         430         440         450
CTAACCTAGG AAGAATTGGT GTGATCACCA
         460         470         480
ACAGAGAGAG GCACCCTGGA TCTTTTGACG
         490         500         510
TGGTTCACGT GAAAGATGCC AATGGCAACA
```

-continued

```
        520         530         540
GCTTTGCCAC TCGACTTTCC AACATTTTTG
        550         560         570
TTATTGGCAA GGGCAACAAA CCATGGATTT
        580         590         600
CTCTTCCCCG AGGAAAGGGT ATCCGCCTCA
        610         620         630
CCATTGCTGA AGAGAGAGAC AAAAGACTGG
        640         650         660
CGGCCAAACA GAGCAGTGGG TGAAATGGGT
        670         680         690
CCCTGGTGAC ATGTCAGATC TTTGTACGTA
        700         710         720
ATTAAAAATA TTGTGGCAGG ATTAATAGC,
``` or

```
         90        100         110         120
GTCC GAACTGATAT AACCTACCCT GCTGGATTCA
        130         140         150
TGGATGTCAT CAGCATTGAC AAGACGGGAG
        160         170         180
AGAATTTCCG TCTGATCTAT GACACCAAGG
        190         200         210
GTCGCTTTGC TGTACATCGT ATTACACCTG
        220         230         240
AGGAGGCCAA GTACAAGTTG TGCAAAGTGA
        250         260         270
GAAAGATCTT TGTGGGCACA AAAGGAATCC
        280         290         300
CTCATCTGGT GACTCATGAT GCCCGCACCA
        310         320         330
TCCGCTACCC CGATCCCCTC ATCAAGGTGA
        340         350         360
ATGATACCAT TCAGATTGAT TTAGAGACTG
        370         380         390
GCAAGATTAC TGATTTCATC AAGTTCGACA
        400         410         420
CTGGTAACCT GTGTATGGTG ACTGGAGGTG
        430         440         450
CTAACCTAGG AAGAATTGGT GTGATCACCA
        460         470         480
ACAGAGAGAG GCACCCTGGA TCTTTTGACG
        490         500         510
TGGTTCACGT GAAAGATGCC AATGGCAACA
        520         530         540
GCTTTGCCAC TCGACTTTCC AACATTTTTG
        550         560         570
TTATTGGCAA GGGCAACAAA CCATGGATTT
        580         590         600
CTCTTCCCCG AGGAAAGGGT ATCCGCCTCA
        610         620         630
CCATTGCTGA AGAGAGAGAC AAAAGACTGG
        640         650         660
CGGCCAAACA GAGCAGTGGG TGAAATGG
``` or

```
        250         260         270
GATCTT TGTGGGCACA AAAGGAATCC
        280         290         300
CTCATCTGGT GACTCATGAT GCCCGCACCA
        310         320         330
TCCGCTACCC CGATCCCCTC ATCAAGGTGA
        340         350         360
ATGATACCAT TCAGATTGAT TTAGAGACTG
        370         380         390
GCAAGATTAC TGATTTCATC AAGTTCGACA
        400         410         420
CTGGTAACCT GTGTATGGTG ACTGGAGGTG
        430         440         450
CTAACCTAGG AAGAATTGGT GTGATCACCA
        460         470         480
ACAGAGAGAG GCACCCTGGA TCTTTTGACG
        490         500         510
TGGTTCACGT GAAAGATGCC AATGGCAACA
        520         530         540
GCTTTGCCAC TCGACTTTCC AACATTTTTG
        550         560         570
TTATTGGCAA GGGCAACAAA CCATGGATTT
        580         590         600
CTCTTCCCCG AGGAAAGGGT ATCCGCCTCA
        610         620         630
CCATTGCTGA AGAGAGAGAC AAAAGACTGG
        640         650         660
CGGCCAAACA GAGCAGTGGG TGAAATGGGT
        670
CCCTGGTGAC ATGTCA.
``` or their complements.

10. A bacterial host transformed with a recombinant DNA comprising the DNA of claim 9.

11. A recombinant DNA useful for enriching mRNA encoding IL-2 comprising a recombinant DNA of the sequence

```
         10         20         30
AAAAAACAAA ACCAAAACAT TCCGAAAATG
         40         50         60
TCCACAGCCT CACGCCTACC TGCCCTTACC
         70         80         90
CTCAGCTCTT GGCTGGGTCT CCCACTATGC
        100        110        120
CCCATCCCTC CTTCCCTCAG AGGCTGGGTG
        130        140        150
CCAGAGGGTG GATGAGAAGA GATTCTCAAA
        160        170        180
GCTGGGCAGG TCCCAGGAAA AGCCACTTGA
        190        200        210
TCGACCTGGG CAGTGAGGGG AAGCAGGGGG
        220        230        240
TGGGGGGTGG GGTGGGGAGG TGGTGGGGGG
        250        260        270
AGCCAGATGA GATGTTCTCC GACATCTACA
        280        290        300
AGATCCGGGA GATCGCGGAC GGGTTGTGCC
        310        320        330
TGGAGGTGGA GGGGAAGATG GTCAGTAGGA
        340        350        360
CAGAAGGTAA CATTGATGAC TCGCTCATTG
        370        380        390
GTGGAAATGC CTCCGCTGAA GGCCCCGAGG
        400        410        420
GCGAAGGTAC CGAAAGCACA GTAATCACTG
        430        440        450
GTGTCGATAT TGTCATGAAC CATCACCTGC
        460        470        480
AGGAAACAAG TTTCACAAAA GAAGCCTACA
        490        500        510
AGAAGTACAT CAAAGATTAC ATGAAATCAA
        520        530        540
TCAAAGGGAA ACTTGAAGAA CAGAGACCAG
        550        560        570
AAAGAGTAAA ACCTTTTATG ACAGGGGCTG
        580        590        600
CAGAACAAAT CAAGCACATC CTTGCTAATT
        610        620        630
TCAAAAACTA CCAGTTCTTT ATTGGTGAAA
        640        650        660
ACATGAATCC AGATGGCATG GTTGCTCTAT
        670        680        690
TGGACTACCG TGAGGATGGT GTGACCCCAT
        700        710        720
ATATGATTTT CTTTAAGGAT GGTTTAGAAA
        730        740        750
TGGAAAAATG TTAACAAATG TGGCAATTAT
        760        770        780
TTTGGATCTA TCACCTGTCA TCATAACTGG
        790        800        810
CTTCTGCTTG TCATCCACAC AACACCAGGA
        820        830        840
CTTAAGACAA ATGGGACTGA TGTCATCTTG
        850        860        870
AGCTCTTCAT TTATTTTGAC TGTGATTTAT
        880        890        900
TTGGAGTGGA GGCATTGTTT TTAAGAAAAA
        910        920        930
CATGTCATGT AGGTTGTCTA AAAATAAAAT
        940
GCATTTAAAC TC
```

-or

```
     310        320        330
A GGGGAAGATG GTCAGTAGGA
     340        350        360
CAGAAGGTAA CATTGATGAC TCGCTCATTG
     370        380        390
GTGGAAATGC CTCCGCTGAA GGCCCCGAGG
     400        410        420
GCGAAGGTAC CGAAAGCACA GTAATCACTG
     430        440        450
GTGTCGATAT TGTCATGAAC CATCACCTGC
     460        470        480
AGGAAACAAG TTTCACAAAA GAAGCCTACA
     490        500        510
AGAAGTACAT CAAAGATTAC ATGAAATCAA
     520        530        540
TCAAAGGGAA ACTTGAAGAA CAGAGACCAG
     550        560        570
AAAGAGTAAA ACCTTTTATG ACAGGGCTG
     580        590        600
CAGAACAAAT CAAGCACATC CTTGCTAATT
     610        620        630
TCAAAAACTA CCAGTTCTTT ATTGGTGAAA
     640        650        660
ACATGAATCC AGATGGCATG GTTGCTCTAT
     670        680        690
TGGACTACCG TGAGGATGGT GTGACCCCAT
     700        710        720
ATATGATTTT CTTTAAGGAT GGTTTAGAAA
     730        740        750
TGGAAAAATG TTAACAAATG TGGCAATTAT
     760        770        780
TTTGGATCTA TCACCTGTCA TCATAACTGG
     790        800        810
CTTCTGCTTG TCATCCACAC AACACCAGGA
     820        830        840
CTTAAGACAA ATGGGACTGA TGTCATCTTG
     850        860        870
AGCTCTTCAT TTATTTTGAC TGTGATTTAT
     880        890        900
TTGGAGTGGA GGCATTGTTT TTAAGAAAAA
     910        920        930
CATGTCATGT AGGTTGTCTA AAAATAAAAT
     940
GCATTTAAAC TC
``` or their complements.

12. A bacterial host transformed with a recombinant DNA comprising the DNA of claim 11.

* * * * *